United States Patent
Hsu et al.

(10) Patent No.: US 11,357,733 B2
(45) Date of Patent: *Jun. 14, 2022

(54) MUCO-ADHESIVE, CONTROLLED RELEASE FORMULATIONS OF LEVODOPA AND/OR ESTERS OF LEVODOPA AND USES THEREOF

(71) Applicant: Impax Laboratories, LLC, Bridgewater, NJ (US)

(72) Inventors: Ann Hsu, Hayward, CA (US); Liang Dong, Hayward, CA (US); Amy Ding, Hayward, CA (US); Suneel Gupta, Hayward, CA (US)

(73) Assignee: Impax Laboratories, LLC, Bridgewater, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/148,320

(22) Filed: Jan. 13, 2021

(65) Prior Publication Data

US 2021/0128480 A1 May 6, 2021

Related U.S. Application Data

(63) Continuation of application No. 16/573,634, filed on Sep. 17, 2019, now Pat. No. 10,987,313, which is a (Continued)

(51) Int. Cl.
*A61K 9/48* (2006.01)
*A61K 9/16* (2006.01)
(Continued)

(52) U.S. Cl.
CPC .......... *A61K 9/4808* (2013.01); *A61K 9/0053* (2013.01); *A61K 9/1652* (2013.01);
(Continued)

(58) Field of Classification Search
None
See application file for complete search history.

(56) References Cited

U.S. PATENT DOCUMENTS 3,891,696 A 6/1975 Bodor et al.
4,021,555 A 5/1977 Seyfried et al.
(Continued)

FOREIGN PATENT DOCUMENTS

EP 0253490 1/1988
EP 0313845 5/1989
(Continued)

OTHER PUBLICATIONS

Summons and Preliminary Non-Binding Opinion of the Opposition Division in the opposition of European Patent No. 2 234 963 dated Dec. 23, 2021.
(Continued)

*Primary Examiner* — Melissa S Mercier
(74) *Attorney, Agent, or Firm* — Florek & Endres PLLC; Martin P. Endres

(57) ABSTRACT

The invention provides a controlled release oral solid formulation comprising (a) a controlled release component comprising core comprising levodopa and/or an ester of levodopa or salts thereof, wherein the core is coated with a layer of a muco-adhesive polymer and externally coated with a layer of an enteric coated polymer; and (b) a decarboxylase inhibitor component.

40 Claims, 7 Drawing Sheets

Schematic Configuration of Enteric-Coated, Muco-adhesive Multiparticulates

Related U.S. Application Data continuation-in-part of application No. 16/360,936, filed on Mar. 21, 2019, now Pat. No. 10,688,058, which is a continuation of application No. 15/092,086, filed on Apr. 6, 2016, now Pat. No. 10,292,935, which is a continuation-in-part of application No. PCT/US2014/059554, filed on Oct. 7, 2014.

(60) Provisional application No. 61/887,762, filed on Oct. 7, 2013.

(51) Int. Cl.
  *A61K 9/50* (2006.01)
  *A61K 31/198* (2006.01)
  *A61K 9/00* (2006.01)
  *A61K 31/216* (2006.01)
  *A61K 45/06* (2006.01)

(52) U.S. Cl.
  CPC .......... *A61K 9/5026* (2013.01); *A61K 9/5042* (2013.01); *A61K 9/5073* (2013.01); *A61K 31/198* (2013.01); *A61K 31/216* (2013.01); *A61K 45/06* (2013.01); *Y02A 50/30* (2018.01)

(56) References Cited

U.S. PATENT DOCUMENTS

| | | | |
|---|---|---|---|
| 4,160,020 A | 7/1979 | Ayer et al. | |
| 4,367,217 A | 1/1983 | Gruber et al. | |
| 4,424,235 A | 1/1984 | Sheth et al. | |
| 4,427,648 A | 1/1984 | Brickl et al. | |
| 4,438,091 A | 3/1984 | Grubet et al. | |
| 4,826,875 A | 5/1989 | Chiesi | |
| 4,839,177 A | 6/1989 | Colombo et al. | |
| 4,849,227 A | 7/1989 | Cho | |
| 4,855,326 A | 8/1989 | Fuisz | |
| 4,900,755 A | 2/1990 | Dempski et al. | |
| 4,938,968 A | 7/1990 | Mehta | |
| 5,051,262 A | 9/1991 | Panoz et al. | |
| 5,135,950 A | 8/1992 | Pippuri et al. | |
| 5,188,840 A | 2/1993 | Iida et al. | |
| 5,446,194 A | 8/1995 | Bäckström et al. | |
| 5,532,274 A | 7/1996 | Wenzel et al. | |
| 5,576,022 A | 11/1996 | Yang et al. | |
| 5,594,030 A | 1/1997 | Conte et al. | |
| 5,624,960 A | 4/1997 | Wenzel et al. | |
| 5,637,320 A | 6/1997 | Bourke et al. | |
| 5,650,169 A | 7/1997 | Conte et al. | |
| 5,652,271 A | 7/1997 | Harris et al. | |
| 5,681,583 A | 10/1997 | Conte et al. | |
| 5,738,874 A | 4/1998 | Conte et al. | |
| 5,773,031 A | 6/1998 | Shah et al. | |
| 5,780,057 A | 7/1998 | Conte et al. | |
| 5,840,756 A | 11/1998 | Cohen et al. | |
| 5,945,424 A | 8/1999 | Schmidt | |
| 6,024,981 A | 2/2000 | Khankari et al. | |
| 6,027,748 A | 2/2000 | Conte et al. | |
| 6,126,969 A | 10/2000 | Shah et al. | |
| 6,183,778 B1 | 2/2001 | Conte et al. | |
| 6,194,000 B1 | 2/2001 | Smith et al. | |
| 6,221,392 B1 | 4/2001 | Khankari et al. | |
| 6,238,699 B1 | 5/2001 | Rubin | |
| 6,294,200 B1 | 9/2001 | Conte et al. | |
| 6,309,666 B1 | 10/2001 | Hatano et al. | |
| 6,372,252 B1 | 4/2002 | Blume et al. | |
| 6,372,254 B1 | 4/2002 | Ting et al. | |
| 6,376,545 B1 | 4/2002 | Levin | |
| 6,500,867 B1 | 12/2002 | Virkki et al. | |
| 6,531,153 B2 | 3/2003 | Seth | |
| 6,602,521 B1 | 8/2003 | Ting et al. | |
| 6,627,223 B2 | 9/2003 | Percel et al. | |
| 6,630,162 B1 | 10/2003 | Nilvebrant et al. | |
| 6,723,348 B2 | 4/2004 | Faham et al. | |
| 6,730,321 B2 | 5/2004 | Ting et al. | |
| 6,733,781 B2 | 5/2004 | Abu-Izza et al. | |
| 6,793,936 B2 | 9/2004 | Devane et al. | |
| 6,797,732 B2 | 9/2004 | Virkki et al. | |
| 6,811,794 B2 | 11/2004 | Burnside et al. | |
| 7,048,945 B2 | 5/2006 | Percel et al. | |
| 7,094,427 B2 | 8/2006 | Han et al. | |
| 8,377,474 B2 | 2/2013 | Hsu et al. | |
| 8,591,913 B2 | 11/2013 | Miyazaki et al. | |
| 10,292,935 B2 * | 5/2019 | Hsu ..................... | A61K 45/06 |
| 10,688,058 B2 * | 6/2020 | Hsu ..................... | A61K 9/1652 |
| 10,973,769 B2 * | 4/2021 | Hsu ..................... | A61K 9/1652 |
| 10,987,313 B2 * | 4/2021 | Hsu ..................... | A61K 9/4808 |
| 2002/0155154 A1 | 10/2002 | Wong et al. | |
| 2003/0147957 A1 | 8/2003 | Licht et al. | |
| 2003/0152628 A1 | 8/2003 | Licht et al. | |
| 2003/0224045 A1 | 12/2003 | Han et al. | |
| 2004/0028613 A1 | 2/2004 | Quay | |
| 2004/0166159 A1 | 8/2004 | Han et al. | |
| 2005/0070608 A1 | 3/2005 | Remenar et al. | |
| 2005/0147670 A1 | 7/2005 | Hsu et al. | |
| 2005/0203185 A1 | 9/2005 | Remenar et al. | |
| 2006/0013875 A1 | 1/2006 | Han et al. | |
| 2006/0018965 A1 | 1/2006 | Moodley et al. | |
| 2006/0045865 A1 | 3/2006 | Jacob et al. | |
| 2006/0057197 A1 | 3/2006 | Han et al. | |
| 2007/0003621 A1 | 1/2007 | Nangia et al. | |
| 2007/0082048 A1 | 4/2007 | Warner | |
| 2007/0148238 A1 | 6/2007 | Nangia et al. | |
| 2007/0190145 A1 | 8/2007 | Venkatesh et al. | |
| 2007/0275060 A1 | 11/2007 | Befumo et al. | |
| 2008/0131492 A1 | 6/2008 | Nangia et al. | |
| 2008/0299204 A1 | 12/2008 | Nangia et al. | |
| 2009/0004229 A1 | 1/2009 | Pastini et al. | |
| 2009/0220611 A1 | 9/2009 | Dargelas et al. | |
| 2010/0298268 A1 | 11/2010 | Hsu et al. | |
| 2010/0331244 A1 | 12/2010 | Miyazaki | |
| 2011/0111024 A1 | 5/2011 | Mao et al. | |
| 2012/0177731 A1 * | 7/2012 | Hsu ..................... | A61K 47/12 424/490 |
| 2013/0195973 A1 | 8/2013 | Gupta et al. | |
| 2016/0287523 A1 | 10/2016 | Hsu et al. | |

FOREIGN PATENT DOCUMENTS

| | | |
|---|---|---|
| EP | 0320051 | 6/1989 |
| EP | 0393572 | 10/1990 |
| EP | 1262198 | 12/2002 |
| EP | 1964566 | 9/2008 |
| EP | 2508174 | 10/2012 |
| WO | 1995001781 | 1/1995 |
| WO | 1999004765 | 2/1999 |
| WO | 99/17745 | 4/1999 |
| WO | 1999017745 | 4/1999 |
| WO | 1999051209 | 10/1999 |
| WO | 2000015197 | 3/2000 |
| WO | 2000018447 | 4/2000 |
| WO | 2002000213 | 1/2002 |
| WO | 2003000018 | 1/2003 |
| WO | 2003005967 | 1/2003 |
| WO | 2003101432 | 12/2003 |
| WO | 2004062577 | 7/2004 |
| WO | 2005023185 | 3/2005 |
| WO | 2005099678 | 10/2005 |
| WO | 2006026556 | 3/2006 |
| WO | 2007002516 | 1/2007 |
| WO | 2007002518 | 1/2007 |
| WO | 2007022956 | 3/2007 |
| WO | 2007090091 | 8/2007 |
| WO | 2009085306 | 7/2009 |
| WO | 2010140531 | 12/2010 |
| WO | 2012136819 | 10/2012 |
| WO | 2015054302 | 4/2015 |

OTHER PUBLICATIONS

Summons and Preliminary Non-Binding Opinion of the Opposition Division in the opposition of European Patent No. 3 054 929 dated Dec. 16, 2021.

(56) References Cited

OTHER PUBLICATIONS

Impax Laboratories, LLC, "A Study to Assess the PK and Pharmacodynamics of IPX203 in Patients With Advanced Parkinson's Disease," ClinicalTrials.gov archive (identifier NCT02271530), Oct. 22, 2014, 9 pages.
Impax Laboratories, LLC, "A Study to Evaluate the Safety and Efficacy of IPX203 in Parkinson's Disease Patients With Motor Fluctuations," ClinicalTrials.gov archive (identifier NCT03670953), Sep. 14, 2018, 7 pages.
Impax Laboratories, LLC, "Open Label Extension (OLE) Study of the Safety and Clinical Utility of IPX203 in PD Patients With Motor Fluctuations," ClinicalTrials.gov archive (identifier NCT038//510), Mar. 15, 2019, 14 pages.
Impax Laboratories, LLC, "A Study to Assess the PK and Pharmacodynamics of IPX203 in Subjects With Advanced Parkinson's Disease," ClinicalTrials.gov archive (identifier NCT03007888) Jan. 2, 2017, 7 pages.
Impax Laboratories, LLC, "An Open-Label Extension Study of the Safety and Clinical Utility of IPX203 in Parkinson's Disease Patients with Motor Fluctuations," Clinicaltrialsregister.eu, EudraCT No. 2018-002234-21 (Germany) May 16, 2019 8 pages.
Impax Laboratories, LLC, "An Open-Label Extension Study of the Safety and Clinical Utility of IPX203 in Parkinson's Disease Patients with Motor Fluctuations," Clinicaltrialsregister.eu, EudraCT No. 2018-002234-21 (Czech Republic) May 30, 2019 8 pages.
FDA Bioequivalence Review for ANDA 75-091 (1998).
Nyholm, et al., "Levodopa Infusion Therapy in Parkinson Disease: State of the Art in 2004." Clinical Neuropharmacology, 27(5): 245-256 (2004).
Nyholm, "Pharmacokinetic Optimisation in the Treatment of Parkinson's Disease: An Update." Clinical Pharmacokinetics, 45(2): 109-136 (2006).
Nyholm et al., "Optimizing Levodopa Pharmacokinetics: Intestinal Infusion Versus Oral Sustained-Release Tablets." Clinical Neuropharmacology, 26(3): 156-163 (2003).
Nykanen et al., "Citric Acid as Excipient in Multiple Unit Enteric-Coated Tablets for Targeting Drugs on the Colon." International Journal Pharmaceuticas, 229(1-2): 155-162 (2001).
Ogawa, "Factors Affecting Levodopa Effects in Parkinson's Disease." Acta Med Okayama, 54(3): 95-101 (2000).
Pinho et al., "Over Expression of Renal LAT1 and LAT2 and Enhanced LDOPA Update in SHR Immortalized Renal Proximal Tubular Cells." Kidney International, 66(1): 216-226 (2004).
Poewe et al., "Treatment of Motor Fluctuations in Parkinson's Disease with an Oral Sustained-Release Preparation of L-Dopa: Clinical and Pharmacokinetic Observations." Clinical Neuropharmacology, 9(5): 430-439 (1986).
Quinones et al., "The Dopamine Precursor L-Dihydroxyphenylalanine is Transported by the Amino Acid Transporters rBAT and LAT2 in Renal Cortex." American Journal of Physiology Renal Physiology, 287(1): F74-80 (2004).
Rao et al., "Parkinson's Disease: Diagnosis and Treatment." American Family Physician, 74(12): 2047-2054 (2006).
Scattergood et al., "Comparative Study of Theoretical Versus Actual Weight Gain for a Surelease® Barrier Membrane on Coated Pellets." www.colorcon.com, mr/poster/SureSpheres/stud_comp_wt_gain REV/Rev1.2009 (2004).
SEIPE et al., "Strategies for the Design of Hydrophilic Matrix Tablets with Controlled Microenvironmental pH." International Journal of Pharmaceutics, 316 (1-2): 14-20 (2006).
Simon et al., "The Effects of a Normal Protein Diet on Levodopa Plasma Kinetics in Advanced Parkinson's Disease." Parkinsonism Related Disorders, 10(3): 137-142 (2004).
Sinemet® Package Insert, 2002.
Tang et al., "Coating of Multiparticulates for Sustained Release." American Journal of Drug Delivery, 3(1): 17-28 (2005).
"Treatment of Early Parkinson's Disease." American Family Physician, 72(3): 497-500 (2005), http://aafp.org/afp/2005/0801/p497.html.
HSU Declaration, Under 37 C.F.R. 1.132 (Sep. 24, 2012).

Bettini et al. "Influence of Layer Position on In Vitro and In Vivo Release of Levodopa Methyl Ester and Carbidopa from Three-Layer Matrix Tablets," European Journal of Pharmaceutics and Biopharmaceutics, 53:227-232 (2002).
Deleu, et al., "Clinical and Pharmacokinetic Comparison of Oral and Dodental Delivery of Levodopa/Carbidopa in Patients with Parkinson's Disease with a Fluctuating Response to Levodopa," European Journal of Clinical Pharmacology, 41:453-458 (1991).
Pahwa et al., "Early Morning Akinesia in Parkinson's Disease: Effect of Standard Carbidopa/Levodopa and Sustained-Release Carbidopa/Levodopa," Neurology, 46: 1059-1062 (1996).
Pahwa et al., "Comparison of Standard Carbidopa-Levodopa and Sustained-Release Carbidopa-Levodopa in Parkinson's Disease: Pharmacokinetic and Quality of Life Measures," Movement Disorders, 12:677-681 (1997).
Kurlan et al., "Duodenal and Gastric Delivery of Levodopa in Parkinsonism," Annals of Neurology, 23:589-595 (1988).
Kurlan et al., "Erratic Gastic Emptying of Lvodopa May Cause Random Fluctuations of Parkinsonian Mobility," Neurology, 38:419-421 (1988).
Baruzz et al., "Influence of Meal Ingestion Time on Pharmacokinetics of Orally Administered Levodopa in Parkinsonian Patients," Clinical Neuropharmacolgy, 10:527-537 (1987).
Sinemet® CR Package Insert, Jan. 2011.
Rytary® Package Insert, Jan. 2015.
Stalevo® Package Insert, Sep. 2010.
FDA Draft Guidance for Carbidopa Levodopa Extended Release Capsule Sep. 2015.
Yao, et al. "Clinical Pharmacokinetics of IPX066: Evaluation of Dose Proportionality and Effect of Food in Healthy Volunteers," Clinical Neuropharmacol., 29:10-17 (2016).
Hsu, et al., "Comparison of the Pharmacokinetics of an Oral Extended-Release Capsule Formulation of Carbidopa-Levodopa (IPX066) with Immediate-Release Carbidopa-Levodopa (Sinemet®), Sustained-Release Carbidopa-Levodopa (Sinemet® CR), and Carbidopa-Levodopa-Entacapone (Stalevo®)" J Clinical Pharmacology 55 (9):995-1001 (2015).
Brooks, "Optimizing Levodopa Therapy for Parkinson's Disease with Levodopa/Carbidopa/Entacapone: Implications from a Clinical and Patient Perspective," Neuropsychiatr Dis Treat 4:39-47 (2008).
Chana, et al., "Delayed Early Morning Turn "ON"in Response to a Single Dose of Levodopa in Advanced Parkinson's Disease: Pharmaconkinetics Should be Considered," J. Neurol Neurosurg Psychiaty 75:1782-1783 (2004).
Hauser, "Levodopa: Past, Present, and Future," Eur. Neurol. 62:1-8 (2009).
Kempster et al., "Levodopa Peripheral Pharmacokinetics and Duration of Motor Response in Parkinson's Disease," J. Neurol Neurosurg Psychiatry, 52:718-723 (1989).
Mao et al., "Population Pharmacodynamics of IPX066: An Oral Extended-Release Capsule Formulation of Carbidopa-Levodopa, and Immediate-Release Carbidopa-Levodopa in Patients with Advanced Parkinson's Disease," J. Clin. Pharm. 53:523-531 (2013).
Fahn, "Parkinson Disease, the Effect of Levodopa and the ELLDOPA Trial, Earlier vs Later L-DOPA," Arch Neurol. 56 (5):529-535 (1999).
Stocchi, et al., "Intermittent vs Continuous Levodopa Administration in Patients with Advanced Parkinson Disease: a Clinical and Pharmacokinetic Study," Arch Neurol. 62(6):905-910 (2005).
Goetz, et al., "Handling Missing Values in the NDS-UPDRS," Mov. Disord. 30(12):1632-1638 (2015).
Modi, et al., "Single-Dose Pharmacokinetics and Pharmacodynamics of IPX203 in PatientsWith Advanced Parkinson Disease: A Comparison with Immediate-Release Carbidopa-Levodopa and with Extended-Release Carbidopa-Levodopa Capsules, "Clinical Neuropharmacology 42(1):4-8 (2019).
Chen, et al., "Pharmacokinetics and Pharmacodynamics of Gastroretentive Delivery of Levodopa/Carbidopa in Patientswith Parkinson Disease," Clin Neuropharmacol 35:67-72 (2012).
Hauser, et al., "Crossover Comparison of IPX066 and a Standard Levodopa Formulation in Advanced Parkinson's Disease," Mov. Disord, 26:2246-2252 (2011).

(56) References Cited

OTHER PUBLICATIONS

Stacy et al., "Motor Effects and Safety of IPX203, an Investigational Extended-Release Formulation of Carbidopa-Levodopa, in Advanced Parkinson's Disease: A Single-Dose Phase 2 Study," Aug. 21, 2017.
Stacy et al., "Motor Effects and Safety of IPX203, an Investigational Extended-Release Formulation of Carbidopa-Levodopa, in Advanced Parkinson's Disease: A Single-Dose Phase 2 Study," Neurology, 2017; 89, e99 (2017 Emerging Science Abstracts), Aug. 21, 2017.
Impax Laboratories, "Impax Laboratories (IPXL) to Present Data on Neurology Development Programs at AAN" StreetInsider com, Apr. 21, 2017.
Pena, "IPX203 Extended-Release Capsules Reduce 'Off' Time In Advanced Parkinson's," parkinsonsnewtoday.com/2019/07/18/ipx203-extended-release-capsules-reuced-off-time-advanced-parkinsons/ Jul. 18, 2019.
Modi et al., "Pharmacodynamics, Efficacy, and Safety of IPX203 in Parkinson Disease Patients With Motor Fluctuations," Clinical Neuropharmacology, 42(5) pp. 149-156 Sep. 2019 (published on line Jul. 12, 2019).
Mittur et al., "Multiple-Dose Pharmacodynamics of IPX203," Annals of Neurology, vol. 84 (suppl 22) 2018, S324LBA (abstract presented during the 143 rd Annual Meeting of American Neurological Association Oct. 21-23, 2018 Atlanta, GA) Oct. 5, 2018.
Impax Laboratories, LLC, "An Randomized Controlled Study to Compare the Safety and Efficacy of IPX203 with Immediate-Release Carbidopa-Levodopa in Parkinson's Disease Patients with Motor Fluctuations," Clinicaltrialsregister.eu, EudraCT No. 2018-002233-37 (UK) Feb. 14, 2019 6 pages.
Impax Laboratories, LLC, "An Randomized Controlled Study to Compare the Safety and Efficacy of IPX203 with Immediate-Release Carbidopa-Levodopa in Parkinson's Disease Patients with Motor Fluctuations," Clinicaltrialsregister.eu, EudraCT No. 2018-002233-37 (Germany) Jan. 8, 2018 6 pages.
Impax Laboratories, LLC, "An Open-Label Extension Study of the Safety and Clinical Utility of IPX203 in Parkinson's Disease Patients with Motor Fluctuations," Clinicaltrialsregister.eu, EudraCT No. 2018-002234-21 (Spain) Jun. 11, 2019 8 pages.
Stacy et al., "Motor Effects and Safety of IPX203, an Investigational Extended-Release Formulation of Carbidopa-Levodopa, in Advanced Parkinson's Disease: A Single Dose Study," Poster presented at the American Academy of Neurology (AAN) Annual Meeting, Boston, MA Apr. 22-28, 2017 (Pos 005).
Stacy et al., "Motor Effects and Safety of IPX203, an Investigational Extended-Release Formulation of Carbidopa-Levodopa, in Advanced Parkinson's Disease: A Single Dose Study," Poster presented at the 21st International Congress of Parkinson's Disease and Movement Disorders, Vancouver, BC, Canada, Jun. 4-7, 2017 (Pos1412).
Mittur et al., "Multiple-Dose Pharmacodynamics of IPX203: A New Investigational Oral Extended-Release Formulation of Carbidopa-Levodopa, in Patients with Advanced Parkinson's Disease," Poster presented at the Annual Meeting of the American Neurological Association, Atlanta, GA, Oct. 21-23, 2018.
Roy et al., "Polymers in Mucoadhesive Drug-Delivery Systems: A Brief Note," Designed Monomers and Polymers 12 (2009) pp. 483-495.
Nyholm, Dag, "Phamacotherapy for Parkinson's Disease—Observations and Innovations," Comprehensive Summaries of Uppsala Dissertations from the Faculty of Medicine 1236, May 2003.
Lewitt, Peter et al., "New Developments in Levodopa Therapy," Neurology, 62(1 suppl. 1):S9-S16, Jan. 2004.
Han, Chien-Hsuan, Declaration Under 37 C.F.R. §1.132, Oct. 14, 2004.
Hiroshi, et al., "The Effect of Ascorbic Acid on the Pharmacokinetics of Levodopa in Elderly Patients with Parkinson's Disease," Clinical Neuropharmacology, Nov. 2004, 27:270-3.
Fincher, "Particle Size of Drugs and its Relationship to Absorption and Activity," Journal of Pharmaceutical Sciences, 1968, 57:1825-35.

Actavis Laboratories FL, Inc., Notification of Certification for U.S. Pat. Nos. 9,089,607 and 9,089,608 Pursuant to § 505(j)(2)(B)(ii) of the Federal Food, Drug, and Cosmetic Act, Aug. 13, 2015.
Actavis Laboratories FL, Inc., Notification of Certification for U.S. Pat. Nos. 8,377,474; 8,557,283; 8,454,998 and 7,094,427 Pursuant to § 505(j)(2)(B)(ii) of the Federal Food, Drug, and Cosmetic Act, Aug. 4, 2015.
Impax Laboratories, Inc., Complaint against Actavis Laboratories FL, Inc. and Actavis Pharma Inc., Action for Patent Infringement under the Food and Drug Laws and Patent Laws of the United States, Sep. 17, 2015.
Mark, et al., "Controlled-Release Carbidopa-Levodopa (Sinemet) in Combination with Standard Sinimet in Advanced Parkinson's Disease," 19 Annals Clinical Laboratory Sci. vol. 19, No. 2, 101-106(1989).
Hoffman, et al., "Pharmacokinetic and Pharmacodynamic Aspects of Gastroretentive Dosage Forms," Intl. J. of Pharmaceutics, 227, 141-153. (2004).
Yeh, et al., "Pharmacokinetics and Bioavailability of Sinimet CR; A Summary of Human Studies," Neurology vol. 39, 25-38 (Supp. 2 1989).
Cedarbaum, et al., "A Pharmacokinetic and Pharmacodynamic Comparison of Sinemet CR (50/200) and Standard Sinimet (25/100)," 39 Neurology 38-44 (Supp. 2 1989).
Grahnen, et al., "Comparative Multiple-Dose Pharmacokinetics of Controlled-Release Levodopa Products," 32 European Neurology 343-348 (1992).
Young, Rosabel, "Update on Parkinson's Disease," 59 American Family Physician vol. 59, 2155-2167 (1999).
Sasahara, et al., "Dosage Form Design for Improvement of Bioavailability of Levodopa II: Bioavailability of Marketed Levodopa Preparations in Dogs and Parkinsonian Patients," Journal of Pharmaceutical Sciences, 69(3), 261-265 (1980).
Klausner, et al., "Novel Levodopa Gastroretentive Dosage Form: In-Vivo Evaluation in Dogs," J. Controlled Release, 88, 117-126 (2003).
Klausner, et al., "Novel Gastroretentive Dosage Form: Evaluation of Gastroretentivity and its Effect on Levodopa Absorption in Humans," Pharm. Res., 20(9), 1466-1473 (2003).
Notification pursuant to Section 505 (j) (2) (B) (iv) of the Federal Food Drug and Cosmetic Act, Feb. 14, 2017.
Akhgari et al. "Statistical Optimization of Indomethacin Pellets Coated with pH-Dependent Methacrylic Polymers for Possible Colonic Drug Delivery." International Journal of Pharmaceutics, 305:22-30 (2005).
Badawy, et al., "Microenvironmental pH Modulation in Solid Dosage Forms." Journal of Pharmaceutical Sciences, vol. 96, No. 5, 948-59 (2007).
Bredenberg et al., "An Automatic Dose Dispenser for Microtablets—A New Concept for Individual Dosage of Drugs in Tablet Form." International Journal Pharmaceutics, 261:137-146 (2003).
Cedarbaum, "Clinical Pharmacokinetics of Anti-Parkinsonian Drugs." Clinical Pharmacokinetics, 13(3): 141-178 (1987).
Cedarbaum, "The Promise and Limitations of Controlled-Release Oral Levodopa Administration." Clinical Neuropharmacology, 12(3): 147-166 (1989).
Chourasia, et al. "Pharmaceutical Approaches to Colon Targeted Drug Delivery Systems." Journal of Pharmacy and Pharmaceutical Sciences, 6(1); 33-66 (2003).
Cole et al., "Enteric Coated HPMC Capsules Designed to Achieve Intestinal Targeting." International Journal Pharmaceutics, 231(1): 83-95 (2002).
Contin et al., "Pharmacokinetic Optimisation in the Treatment of Parkinson's Disease." Clinical Pharmacokinetics, Jun. 30(6): 463-481 (1996).
Crevoisier et al., "Bioavailability of L-Dopa after Madopar HBS Administration in Healthy Volunteers." European Neurology, 27 (Suppl. 1): 36-46 (1987).
Crevoisier et al., "Comparative Single—and Multiple-Dose Pharmacokinetics of Levodopa and 3-O-Methyldopa Following a New Dual-Release and a Conventional Slow-Release Formulation of Levodopa and Benserazide in Healthy Volunteers." European Neurology, 49(1): 39-44 (2003).

(56) References Cited

OTHER PUBLICATIONS

Dave et al., "Expression of Heteromeric Amino Acid Transporters along the Murine Intestine." J Physiol 558.2, 597-610 (2004).
Dingemanse, et al. "Pharmacokinetic Studies with a Dual-Release Formulation of Levodopa, a Novel Principle in the Treatment of Parkinson's Disease." European Neurology, 39(2): 119-124 (1998).
Espinoza et al., "Influence of Admixed Citric Acid on the Release Profile of Pelanserin Hydrochloride from HPMC Matrix Tablets" International Journal Pharmaceutics, 201(2): 165-173 (2000).
Gomes, et al.,"Na+ Independent Transporters, LAT-2 and B0,+, Exchange L-DOPA with Neutral and Basic Amino Acids in Two Clonal Renal Cell Lines." Journal Membrane Biology, 186(2): 63-80 (2002).
Gomes, et al., "L-DOPA Transport Properties in an Immortalised Cell Line of Rat Capillary Cerebral Endothelial Cells, RBE 4." Brain Research, 829 (1-2): 143-150 (1999).
Goole et al., "Developmental and Evaluation of New Multiple-Unit Levodopa Sustained-Release Floating Dosage Forms" International Journal of Pharmaceutics, 334(1-2): 35-41 (2007).
Goole et al., "Evaluation and Floating Enhancement of Levodopa Sustained Release Floating Minitablets Coated with Insoluble Acrylic Polymer." Drug Development and Industrial Pharmacy, 34(8): 827-833 (2008).
Guthmann et al., "Development of A Multiple Unit Pellet Formulation for a Weakly Basic Drug." Drug Development and Industrial Pharmacy, 33(3): 341-349 (2007).
Horter, et al., "Influence of Physicochemical Properties on Dissolution of Drugs in the Gastrointenstinal Tract." Advance Drug Delivery Reviews, 46(1-3): 75-87 (2001).
Ilda, et al., "Improvement of Intestinal Absorption of P-glycoprotein Substrate by D-Tartaric Acid." Drug Metabolism and Pharmacokinetics, 21(5): 424-428 (2006).
Jenner, "Avoidance of Dyskinesia: Preclinical Evidence for Continuous Dopaminergic Stimulation." Neurology, 62 (Suppl. 1): S47-55 (2004).
Kendall, et al., "The Role of Polymers in Solid Oral Dosage Forms." Polymers in Drug Delivery, 35-48 (Ijeoma F. Uchebbo and Andres G Schatzlein eds., 2006).
Khor, et al., "The Pharmacokinetics and Pharmacodynamics of Levodopa in the Treatment of Parkinson's Disease." Current Clinical Pharmacology, 2(3): 234-243 (2007).
Knop, et al., "Pharmaceutical Pellets." ExAct, No. 15 (Nov. 2005).
Kranz, et al., "Development of a Single Unit Extended Release Formulation for Zk 811 752, a Weakly Basic Drug." European Journal of Pharmaceutics Sciences, 26(1): 47-53 (2005).
Lees, "The On-Off Phenomenon." Journal of Neurology, Neurosurgery, and Psychiatry, Special Supplement 29-37 (1989).
Lewitt, "Clinical Studies with and Pharmacokinetic Considerations of Sustained-Release Levodopa." Neurology, 42 (Suppl. 1): 29-32 (1992).
Lewitt, "Levodopa Therapeutics: New Treatment Strategies." Neurology, 43 (Suppl. 6): S31-37 (1993).
Li et al., "Enteric-Coated Layered Double Hydroxides as a Controlled Release Drug Delivery System." International Journal of Pharmaceutics, 287(1-2): 89-95 (2004).
Lorenzo-Lamosa et al., "Design of Microencapsulated Chitosan Microspheres for Colonic Drug Delivery." Journal at Control Release, 52 (1-2): 109-118 (1998).
Macmahon et al., "A Comparison of the Effects of Controlled-Release Levodopa (Madopar CR) with Conventional Levodopa in late Parkinson's Disease" Journal of Neurology, Neurosurgery, and Psychiatry, 53(3): 220-223 (1990).
Malcom et al., "Single-Dose Pharmacokinetics of Madopar HBS in Patients and Effect of Food and Antacid on the Absorption of Madopar HBS in Volunteers," European Neology, 27 (Suppl. 1): 28-35 (1987).
Opposition submission against European Patent No. 2 234 963 filed by Dr. Luigi Rumi, Jan. 7, 2021.

Hayashi et al., "Physiological Mechanism for Enhancement of Paracellular Drug Transport," Journal of Controlled Release 62 (1999) pp. 141-148.
Nagayama et al., "Effect of Ascorbic Acid on the Pharmacokinetics of Levodopa in Elderly Patients with Parkinson Disease," Clin. Neuropharmacol., vol. 27, No. 6, Nov.-Dec. 2004, pp. 270-273.
Opposition submission against European Patent No. 2 234 963 filed by Teva Pharmaceutical industries, Limited, Jan. 7, 2021.
Carbidopa and Levodopa Tablet, extended release, Package Insert, Mylan Pharmaceuticals Inc., Feb. 2020 revision (original publication 1999).
Lewitt et al., "Controlled-Release Carbidopa/Levodopa (Sinemet 50/200 CR4) Clinical and Pharmacokinetic Studies," Neurology 1989; 39 (Suppl. 2); pp. 45-53.
Response to Oppositions of European Patent No. 2 234 967 filed by Impax Laboratories LLC Jun. 8, 2021.
Goodman & Gilman's: The Pharmacological Basis of Therapeutics, 9th ed. (1996), pp. 509-511.
Opposition submission against European Patent No. 3 054 929 filed by Dr. Luigi Rumi, May 5, 2021.
Response to opposition of European Patent No. 3 054 929 dated Sep. 17, 2021.
Response to opposition of European Patent No. 2 234 963 dated Jun. 8, 2021.
INBRIJA (levodopa inhalation powder) Prescribing Information, Dec. 2018.
INBRIJA (levodopa inhalation powder) Prescribing Information, Aug. 2020.
Impax Laboratories, LLC, "A Study to Evaluate the Safety and Efficacy of IPX203 in Parkinson's Disease Patients With Motor Fluctuations," ClinicalTrials.gov archive (identifier NCT03670953), Jul. 26, 2021 update, 7 pages.
PCT International Search Report for PCT/US2014/059554, dated Jan. 13, 2015.
PCT International Written Opinion for PCT/US2014/059554, dated Jan. 13, 2015.
PCT International Preliminary Report on Patentability for PCT/US2014/059554, dated Apr. 12, 2016.
Armstrong et al., Diagnosis and Treatment of Parkinson's Disease: A Review. JAMA. Feb. 2020;323:548-560.
Bibbiani et al., "Continuous Dopaminergic Stimulation Reduces Risk of Motor Complications in Parkinsonian P," Exp Neurol. Jan. 2005;192(1):73-8.
Cilia et al., "The Modern Pre-Levodopa Era of Parkinson's Disease: Insights Into Motor Complications From Sub-Saharan Africa," Brain Jul. 2014;137(10):2731-42.
Freitas et al., "Motor Complications of Dopaminergic Medications in Parkinson's Disease," Semin Neurol. Apr. 2017;37:147-157.
Jankovic et al., "Therapies in Parkinson's Disease," Curr Opin Neurol. Aug. 2012;25(4):433-47.
LeWitt et al., "Levodopa Therapy for Parkinson Disease a Look Backward and Forward," Neurology. Apr. 2016;86 (Suppl 1):S3-12.
Mittur et al., "Pharmacokinetics of Rytary, an Extended-Release Capsule Formulation of Carbidopa-Levodopa," Clin Pharmacokinet. Feb. 2017;56:999-1014.
Nilsson et al., "Duodenal Levodopa Infusion in Parkinson's Disease-Long-Term Experience," Acta Neurologica Scandinavica. Jun. 2001;104:343-348.
Nyholm et al., "Duodenal Levodopa Infusion Monotherapy vs Oral Polypharmacy in Advanced Parkinson Disease," Neurology Jan. 2005;64:216-223.
Olanow et al. "Double-Blind, Double-Dummy, Randomized Study of Continuous Intrajejunal Infusion of Levodopa-Carbidopa Intestinal Gel in Advanced Parkinson's Disease," Lancet Neurol. Feb. 2014;13:141-149.
Othman et al., "Levodopa-Carbidopa Intestinal Gel Pharmacokinetics: Lower Variability Than Oral Levodopa-Carbidopa," J Parkinson's Dis. Jan. 2017;7:275-8.
Pfeiffer et al. "Clinical Implications of Gastric Complications on Levodopa Treatment in Parkinson's Disease," Parkinsonism Relat Disord May 2020;76:63-71.

(56) References Cited

OTHER PUBLICATIONS

Stocchi et al., "Intermittentvs Continuous Levodopa Administration in Patients with Advanced Parkinson Disease: a Clinical and Pharmacokinetic Study," Arch Neurol. Jun. 2005:62(6):905- 910.

Zhang et al., "The Advantages of Levodopa-Carbidopa Intestinal Gel for Patients with Advanced Parkinson's Disease: a Systematic Review," Drug Des Devel Ther. Feb. 2020;14:845-54.

PCT International Search Report for PCT/US2021/064693, dated Mar. 17, 2022.

PCT International Written Opinion for PCT/US2021/064693, dated Mar. 17, 2022.

Margolesky et al., "Extended-Release Oral Capsule of Carbidopa-Levodopa in Parkinson Disease," Therapeutic Advances in Neurological Disorders 2018, vol. 11, pp. 1-12.

\* cited by examiner

Figure 1: Schematic Configuration of Enteric-Coated, Muco-adhesive Multi-particulates
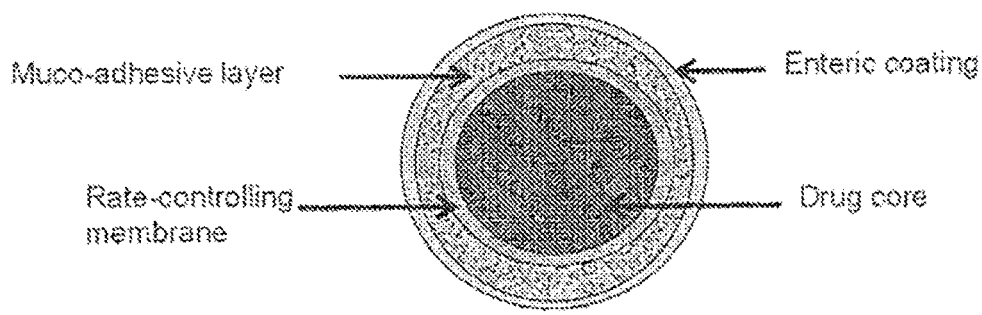

Figure 2: *In-vitro* Dissolution Profiles of IPX203 LDEE-S Formulations
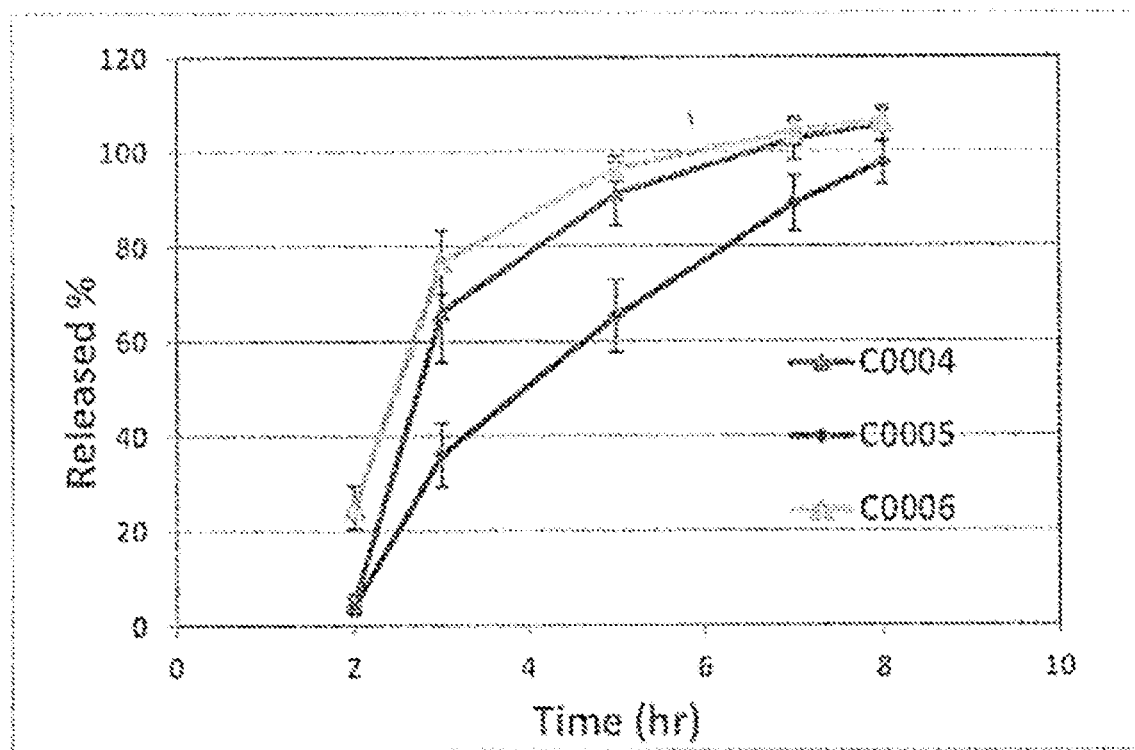
Note: Dissolution method is USP Apparatus 1 with basket speed of 75 rpm in pH 1.0 for 120 min then switch to pH 7 phosphate buffer.

Figure 3: LD Mean Plasma Concentration Profiles of IPX203 Capsules and Sinemet CR Tablet
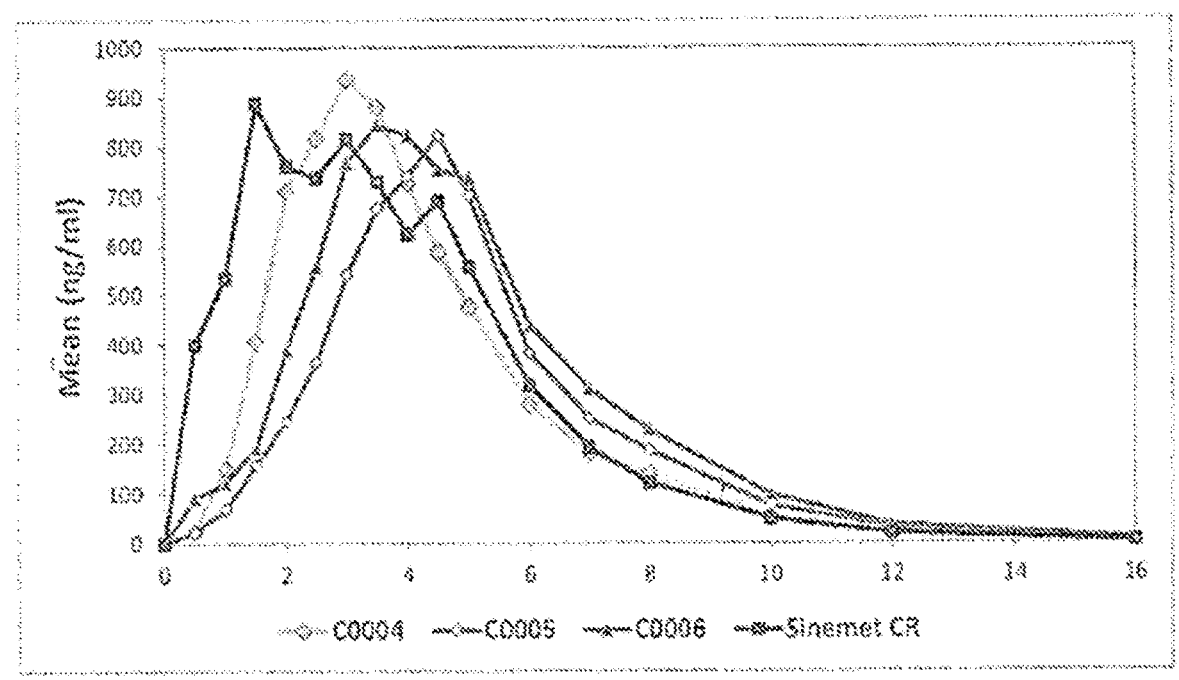

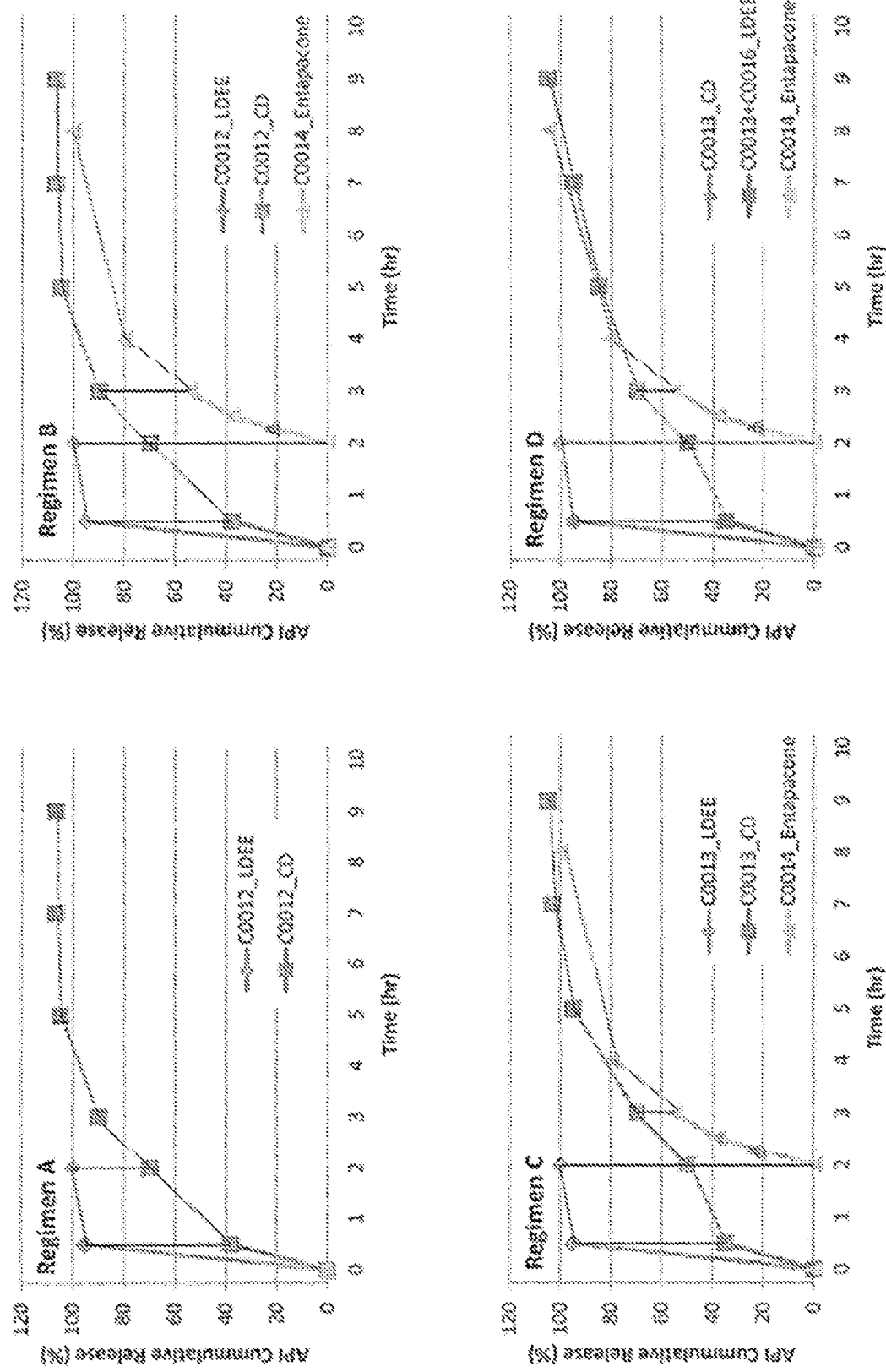
Figure 4: *In-vitro* Release Profiles

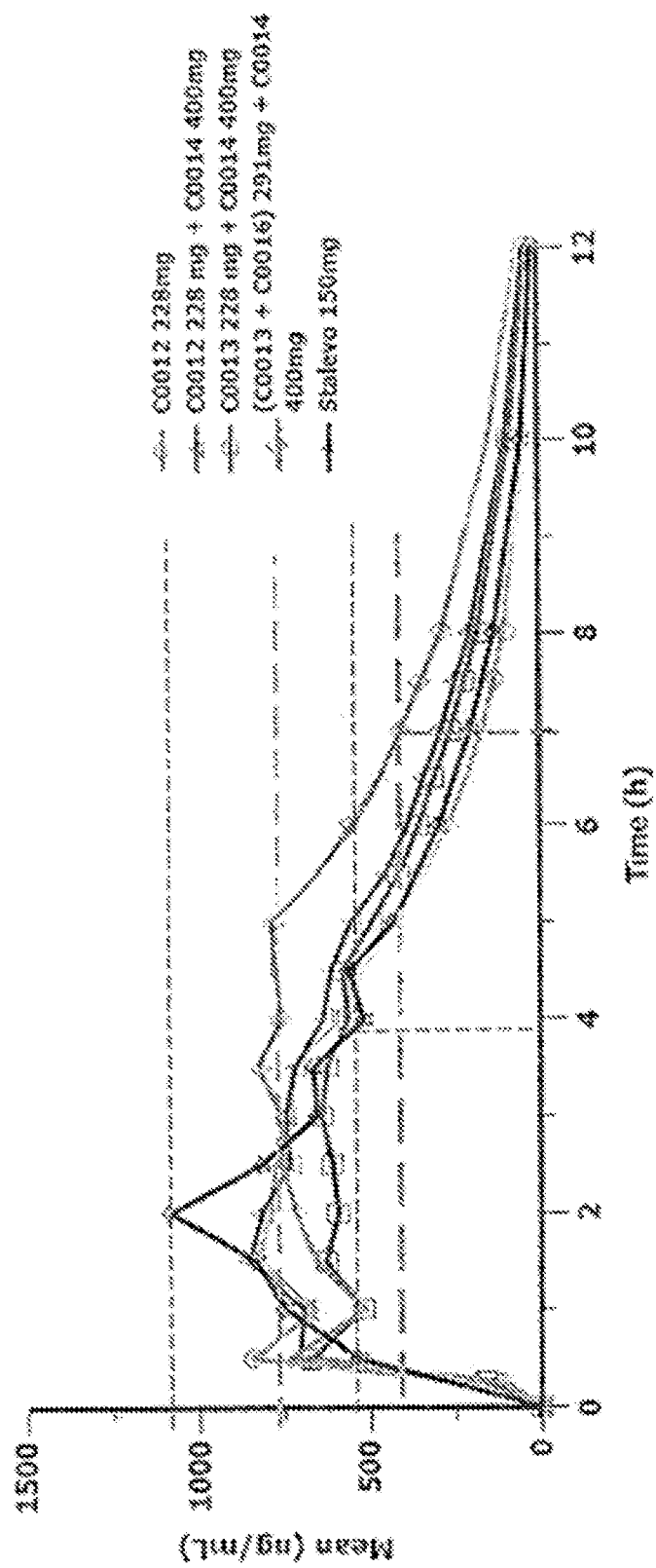
Figure 5: *In-vivo* Levodopa Plasma Profiles

Figure 6: *In-vitro* Release profiles of IPX203-C0023, -C0024, -C0025, -C0026 Formulations
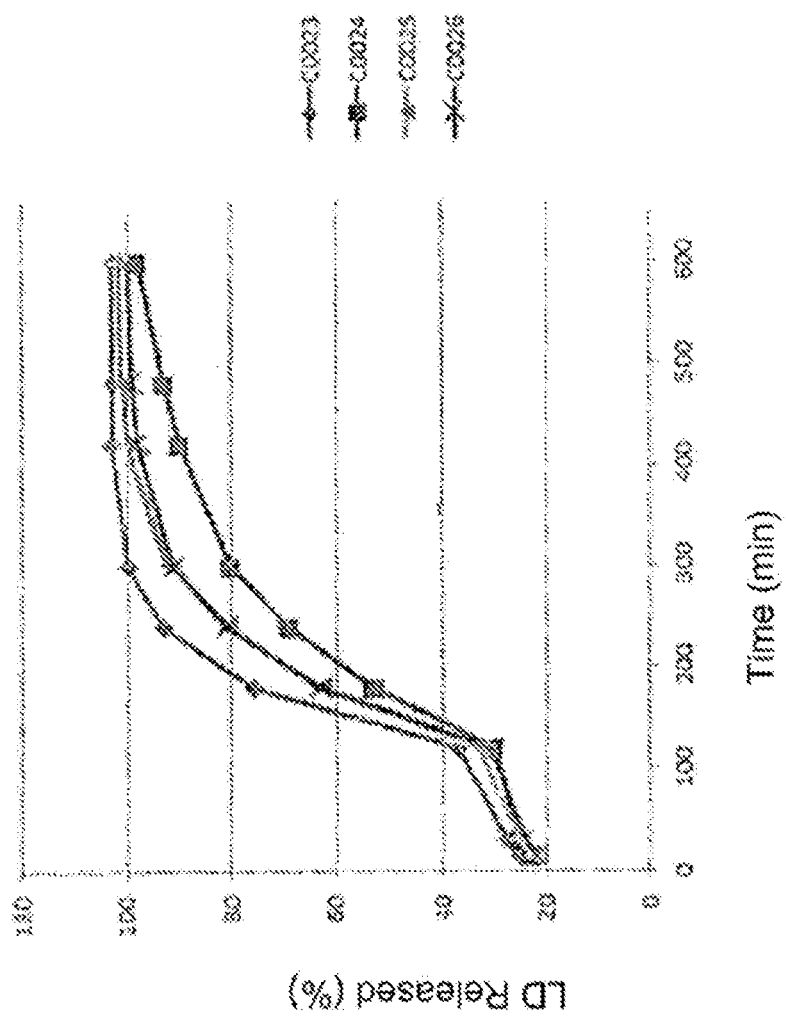

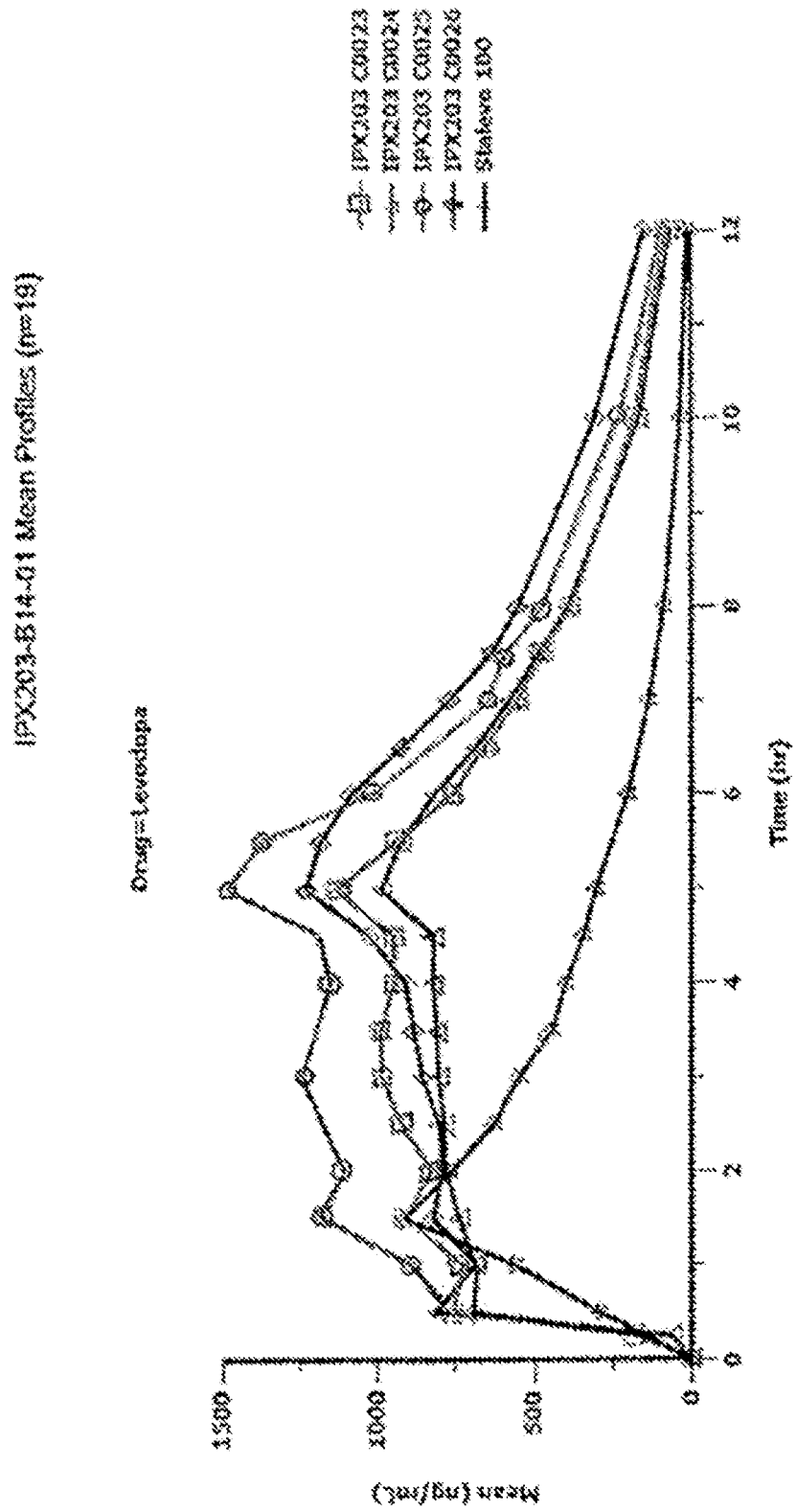
Figure 7: In-vivo Levodopa Plasma Profiles for All the Formulations Tested in IPX203-B14-01 PK Study

MUCO-ADHESIVE, CONTROLLED RELEASE FORMULATIONS OF LEVODOPA AND/OR ESTERS OF LEVODOPA AND USES THEREOF

This application is a continuation of U.S. patent application Ser. No. 16/573,634 filed on Sep. 17, 2019 which is a continuation in part of U.S. patent application Ser. No. 16/360,936 filed on Mar. 21, 2019, now U.S. Pat. No. 10,688,058, which is a continuation of U.S. patent application Ser. No. 15/092,086 filed on Apr. 6, 2016, now U.S. Pat. No. 10,292,935, which is a continuation in part application of PCT Application No. PCT/US2014/059554 filed Oct. 7, 2014, which claims the benefit of U.S. Ser. No. 61/887,762 filed on Oct. 7, 2013, the contents of all of which are hereby incorporated by reference in their entireties into the present application.

Throughout this application, various publications are referenced. The disclosures of these publications in their entireties are hereby incorporated by reference into this application in order to more fully describe the state of the art to which this invention pertains.

FIELD OF THE INVENTION

The present invention relates to controlled release pharmaceutical compositions of levodopa (LD) and esters of LD or salts thereof, formulated with a muco-adhesive material and an enteric material and, optionally, with a rate-controlling material, to yield enhanced drug delivery attributes. These formulations are useful for the treatment of conditions such as neurological diseases associated with reduced or impaired dopamine levels. The formulations are also useful in treating patients with Parkinson's disease (hereinafter "PD").

BACKGROUND OF THE INVENTION

Patients suffering from PD frequently have periods in which their mobility becomes difficult, often resulting in an inability to move. Abnormally low levels of dopamine, a neurotransmitter that affects mobility and control of the skeletal-muscular system, is commonly believed to be the main cause of these motor symptoms in PD patients. However, administration of dopamine is not effective to treat the motor symptoms of Parkinson's disease because dopamine does not cross the blood-brain barrier. To resolve this problem, PD patients are administered LD, the metabolic precursor of dopamine, but LD is not without its issues.

Over time patients treated with LD exhibit symptoms of "wearing off," where a single dose of LD no longer lasts as long as in the early days of LD therapy (usually 5-10 years after start of LD therapy). Such patients may develop motor fluctuations characterized by end-of-dose failure, peak dose dyskinesia, and akinesia. The advanced form of motor fluctuations (also commonly referred to as the 'on-off' phenomenon) is characterized by unpredictable swings from mobility to immobility. Although the causes of these motor fluctuations are not completely understood, advanced patients generally benefit from treatment regimens that produce steady plasma levels of LD, such as through intestinal infusion of LD as such delivery method may mimic normally tonic endogenous dopamine. However, intestinal infusion of LD is restrictive, invasive and cumbersome. Oral delivery of LD is preferred, but plasma concentration levels remain difficult to control via oral delivery.

Combinations of LD and a decarboxylase inhibitor (typically carbidopa (CD)) to treat PD are known in the pharmaceutical arts. Currently, several formulations containing a combination of LD and CD are commercially available, e.g., SINEMET®, SINEMET® CR, STALEVO®, PARCOPA®, RYTARY® and their corresponding generic products. In addition, a decarboxylase inhibitor approved for use outside of the United States, is benserazide, which may be given in combination with LD.

Nonetheless, a need remains for an oral LD formulation that provides steadier plasma concentrations of LD with minimal 'peak-to-trough' fluctuations during daily dosing and that yields a longer duration-of-effect than the commercially available oral dosage forms of LD. In addition, it is desirable for an oral LD formulation to provide therapeutic blood levels of LD quickly, thereby providing a rapid "on" to a PD patient in need thereof.

SUMMARY OF THE INVENTION

The current invention provides controlled release/extended absorption oral dosage forms comprising LD and/or an ester of LD or salts thereof for treatment of PD and other dopamine deficiency disorders. More specifically, in some embodiments, the dosage form comprises at least two components: (i) a first component or immediate release component that provides immediate release of LD and/or an ester of LD or salts thereof; and (ii) a second component or controlled release component that provides for a controlled or sustained release of LD and/or an ester of LD or salts thereof. In certain embodiments, the second component or controlled release component comprises a core containing LD and/or an ester of LD or salts thereof that is mixed, coated or layered with a muco-adhesive material, preferably a muco-adhesive polymer and externally coated with an enteric material, preferably an enteric polymer. The second component or controlled release component may also contain a rate controlling material that will contribute to the controlled release of the LD and/or an ester of LD or salts thereof. The rate controlling material may be part of the controlled release component. For example, the rate controlling material may be a rate controlling polymer applied to the drug containing core and as an undercoating to a coating or layer containing a muco-adhesive material or the rate controlling material may mixed with the LD and/or an ester of LD or salts thereof to form a controlled release matrix or controlled release core of the controlled release component. The second or controlled release component is essential to provide extended absorption, thereby providing prolonged and steady therapeutic coverage.

The oral dosage forms of the present invention may also comprise a decarboxylase inhibitor, such as CD. The decarboxylase inhibitor, such as CD, may be present in the first or immediate release LD component, the second or controlled release LD component or in both the first or immediate release LD component and second or controlled release LD component. The decarboxylase inhibitor, such as CD, may also be present in a component that is separate and distinct from the first or immediate release LD component and/or the second or controlled release LD component. More specifically, one embodiment of the controlled release extended absorption oral dosage form of the present invention may comprise: (i) a first or immediate release component comprising LD; and (ii) a second or controlled release component comprising LD. Another embodiment may comprise: (i) a first or immediate release component comprising LD and CD; and (ii) a second or controlled release component comprising LD. A further embodiment may comprise: (i) a first or immediate release component comprising LD; and (ii) a second or controlled release component comprising LD and CD. A still further embodiment may comprise: (i) a first or immediate release component comprising LD and CD; and (ii) a second or controlled release component comprising LD and CD. Another embodiment may comprise (i) a first or immediate release component comprising LD; and (ii) a second or controlled release component comprising LD. (iii) a third or immediate release component comprising CD; and/or (iv) a fourth or controlled release component comprising CD.

The first, second, third and/or forth components may be separate and distinct components or may be combined to form distinct parts or regions of a larger combined component. For example, the first or immediate release component may comprise a powder or granules comprising LD and/or CD and optionally one or more pharmaceutically acceptable excipients and the powder or granules are a separate and distinct composition from the second or controlled release component however both may be incorporated into a capsule for administration to a patient. Alternatively, the first or immediate release component may comprise a coating or layer comprising LD and/or CD and optionally one or more pharmaceutically acceptable excipients wherein the coating or layer is applied to or part of the second or controlled release component. In this alternative embodiment, the first or immediate release component is combined with the second or controlled release component to form a distinct part or component of the larger combined component. It will be appreciated by the skilled artisan that the location, structure and/or placement of the first or immediate release component with respect to the second or controlled release components in the final dosage form is not critical provided the first or immediate release component allows for the immediate release of the drug such as LD and/or CD following administration of the dosage form to a patient and the second or controlled release component has the muco-adhesive and modified release properties described herein.

The controlled release/extended absorption oral dosage forms of the present invention are useful in treating patients with reduced or impaired dopamine levels, including but not limited to patients with PD.

BRIEF DESCRIPTION OF THE FIGURES

FIG. 1 shows the schematic configuration of the enteric-coated, muco-adhesive controlled release multi-particulates of this invention.

FIG. 2 is a line graph showing the in vitro dissolution profiles of IPX203 multi-particulate 10 formulations IPX203-C0004, IPX203-C0005 and IPX203-C0006.

FIG. 3 shows the plasma profile for IPX203 multi-particulate formulations IPX203-C0004, IPX203-C0005 and IPX203-C0006 in comparison with Sinemet® CR.

FIG. 4 are line graphs showing in vitro release profiles of test regimens A-D for IPX203-B13-01.

FIG. 5 is a line graph showing in vivo levodopa plasma profiles of IPX203 formulations that provide plasma profiles with levodopa levels maintained at or greater than ½ $C_{max}$ longer than about 6 hours under fasted conditions.

FIG. 6 shows in vitro release profiles of IPX203-C0023, -C0024, -C0025 and -C0026 formulations.

FIG. 7 shows in vivo levodopa plasma profiles for the formulations tested in IPX203-B14-01 PK study under fasted conditions.

DETAILED DESCRIPTION OF THE INVENTION

Unless defined otherwise, all technical and scientific terms used herein have the same meaning as commonly understood by one of ordinary skill in the art to which the present disclosure belongs. As used herein the following terms have the following meanings:

As used herein, the term "about" when used before a numerical designation, e.g., temperature, time, amount, concentration, and such other, including a range, indicates approximations which may vary by (+) or (−) 10%, 5% or 1%.

As used herein the term "component" is used in its broadest conventional interpretation unless dictated by context or specifically stated. More specifically, a component may be an element, a constituent part, a single ingredient or a mixture of ingredients. For example, an immediate release component may include a single ingredient such as a drug itself or it may be a combination of a drug and one or more pharmaceutically acceptable excipients provided the "immediate release component" will release the drug immediately upon administration.

It must be noted that as used herein and in the appended claims, the singular forms "a," "an," and "the" include plural referents unless the context clearly dictates otherwise. Thus, for example, reference to "a formulation" includes a plurality of compounds.

Compositions of the Invention

The invention provides controlled release oral solid formulations of LD and/or an ester of LD or a salt thereof providing a relatively steady LD plasma or serum concentration profile over a prolonged period of time and enhancing absorption of the active agents in the gastrointestinal tract of a subject. Without being limited by any one theory, it is believed that the outer enteric coating of the controlled release component will delay release of the active agents or drugs from the controlled release component until the controlled release component has passed through the patient's stomach and into the small intestine. In the small intestine, the outer enteric coating will dissolve and expose the inner muco-adhesive material that facilitates adhesion of the controlled release component to the intestinal mucosa, thereby prolonging or delaying passage of the controlled release component through the intestine and improving absorption. It is desirable to retain the controlled release component within the small intestine, preferably the upper regions of the small intestine, where LD is absorbed most efficiently.

In some embodiments, the controlled release component comprises a rate controlling material, which may be the same or different from the muco-adhesive material. The rate controlling material and/or the muco-adhesive material slows or prolongs the release of active agent(s) or drug(s) from the controlled release component, thereby further extending the release and absorption of drug(s), preferably LD and optionally CD. The controlled release component should release the drug(s) such as LD or CD over a four to ten hour period preferably a five to eight hour period.

The immediate release component should provide fast release of the drug(s) such as LD and CD and thereby a rapid absorption of the drug(s) such as LD and CD. The rapid absorption is important for PD patients in need of a fast "on." As a result, dosage forms of the present invention can provide LD plasma levels that rise quickly, preferably to therapeutic levels, and extend for a prolonged period of time.

In certain embodiments the amount of immediate release LD, and/or its esters or salts thereof should range from about 10% to about 40% based on the total amount of LD and/or its esters or salts thereof in the oral dosage forms, preferably about 15% to 35%, and most preferably about 20%, 21%, 22%, 23%, 24%, 25%, 26%, 27%, 28% 29% or 30%.

Decarboxylase inhibitors such as CD are often provided with LD formulations in order to inhibit decarboxylation of LD, thereby increasing the LD bioavailability. In the dosage forms of the present invention, a decarboxylase inhibitor may be included in the immediate release component, the controlled release component, both the immediate release and controlled release component or in separate immediate release and/or controlled release components as described previously. Preferably, the decarboxylase inhibitor is CD and is included only in an immediate release form such as in the immediate release component with the LD or in a separate immediate release component from the LD. In alternative embodiments, the decarboxylase inhibitor, preferably CD, is included in both an immediate release form as previously described and a controlled release form such as in the controlled release component with the LD or in a separate controlled release component that does not contain LD. In the various embodiments the amount of immediate release decarboxylase inhibitor, preferably CD, should range from about 75% to about 100% based on the total amount of decarboxylase inhibitor in the oral dosage forms, preferably about 80% to 100%, and most preferably about 81%, 82%, 83%, 84%, 85%, 86%, 87%, 88%, 89%, 90%, 91%, 92%, 93%, 94%, 95%, 96%, 97%, 98%, 99% or 100%.

In one embodiment of the invention, the oral dosage forms comprise (1) one or more controlled release components comprising LD and/or an ester of LD or salts thereof and (2) one or more immediate release components comprising LD and/or an ester of LD or salts thereof. The one or more controlled release components may be formulated as a tablet, mini-tablet, bead, pellet, granule or combination thereof. The controlled release components may comprise a core containing LD and/or an ester of LD or salts thereof coated with a layer comprising a muco-adhesive material or polymer and further coated with an outer layer comprising an enteric material or polymer. In certain embodiments, the drug-containing core of the controlled release component will comprises a rate controlling material, which may be mixed with the drug to form a controlled release matrix core, coated onto the drug containing core to form an undercoat below the coating or layer comprising the muco-adhesive material, incorporated into the coating or layer comprising the muco-adhesive material or polymer, or a combination thereof. In some embodiments, the controlled release material and muco-adhesive material may be mixed together with the LD and/or an ester of LD or salts thereof to form a controlled release/muco-adhesive core.

The immediate release component may be formulated as a powder, coating, tablet, mini-tablet, bead, pellet, granule or combination thereof that is separate from or part of the controlled release component. In certain embodiments, the immediate release component is in the form of a powder, tablet, mini-tablet, pellet, bead or granule that is separate from the controlled release component. In alternative embodiments the immediate release component may also be applied as an immediate release coating or layer onto one or more of the controlled release components. In certain embodiments, the immediate release component may be applied to or surround the enteric coating of the controlled release component.

In another embodiment of the invention, the oral dosage forms comprise (1) one or more controlled release components comprising a LD and/or an ester of LD or salts thereof and (2) one or more immediate release components comprising LD and/or an ester of LD or salts thereof and (3) a decarboxylase inhibitor component, preferably a CD component. The decarboxylase inhibitor component may be formulated as a powder, coating, tablet, mini-tablet, bead, pellet, granule or combination thereof. The decarboxylase component may be in an immediate release form, a controlled release form or immediate release and controlled release forms. The decarboxylase inhibitor may be co-formulated with (1) one or more of the controlled release components comprising a LD and/or an ester of LD or salts thereof and/or (2) with one or more of the immediate release components comprising LD and/or an ester of LD or salts thereof. Alternatively the decarboxylase inhibitor may be formulated separately from the one or more controlled release components comprising a LD and/or an ester of LD or salts thereof and/or the one or more immediate release components comprising LD and/or an ester of LD or salts thereof.

The controlled release component may comprise drug-containing cores containing both LD and/or an ester of LD or a salt thereof and a decarboxylase inhibitor such as CD, or the LD and/or ester of LD or salt thereof may be in separate controlled release components from that containing the decarboxylase inhibitor. In one embodiment of the invention, the controlled release component comprises an LD-containing core free or substantially free of a decarboxylase inhibitor such as CD. In this embodiment, substantially free means 15% or less of the total amount of decarboxylase inhibitor in the dosage form is in the controlled release component(s), preferably 10% or less, 9% or less, 8% or less, 7% or less, 6% or less, 5% or less, 4% or less, 3% or less, 2% or less, or 1% or less. The immediate release component of this embodiment may comprise a combination of LD and/or an ester of LD or a salt thereof and a decarboxylase inhibitor. The LD and/or ester of LD or salt thereof may also be in a separate immediate release component from the decarboxylase inhibitor.

In a preferred embodiment of the invention, the oral dosage forms comprise (1) one or more controlled release components comprising LD and/or ester of LD or salt thereof and (2) one or more immediate release components comprising LD and/or ester of LD or salt thereof and CD. In this embodiment, the controlled release component may comprise a drug-containing core coated with a first layer comprising a rate controlling material or polymer, a second layer comprising a muco-adhesive material or polymer and an outer or third layer comprising an enteric material or polymer (see, e.g., FIG. 1). Additional coatings or layers such as cosmetic coatings or non-functional coatings such as water soluble seal coatings can also be added to separate the core, first, second and/or third layers or to overcoat the third layer. These cosmetic or non-functional coatings may also be used to separate an immediate release component from the controlled release component as well as to apply or adhere an immediate release component to the controlled release component. As used herein a non-functional or cosmetic coating should dissolve within 30 minutes, 25 minutes, 20 minutes, 15 minutes, 10 minutes or 5 minutes when the composition with the non-functional or cosmetic coating as the outer most coating is placed in a USP dissolution apparatus, either a Type I or II with 500-900 ml of an aqueous media with a pH of 1-7.

In accordance with the practice of the invention, the components of the invention may be obtained by any methods commonly used in the art such as blending, mixing, granulation and/or coating processes, including, but not limited to, wet-granulation, fluid bed granulation/coating, or extrusion/spheronization, as are well-known in the pharmaceutical arts. The compositions may also be formed with other conventional formulation techniques such as compression and/or slugging. In addition to drugs such as LD and CD, the controlled release components and/or the immediate release components may further contain conventional pharmaceutically acceptable excipients such as lubricants, fillers, binders, disintegrants, glidants, surfactants (sometimes referred to as wetting agents), pH adjusting agents, antioxidants or mixtures of the foregoing.

In an embodiment of the invention, the controlled release and/or immediate release components are multiparticulates that are encapsulated, preferably in a hard gelatin capsule. The multiparticulates may be in a form that can be sprinkled directly onto food or liquids for easy ingestion.

The active agents, such as CD, LD and/or LD esters and salts thereof, may be combined and dispersed throughout the drug-containing core. In another embodiment, the active agents may be present in the center of the drug-containing core or layered/coated on an inert core such as a sugar sphere, microcrystalline cellulose sphere, glass sphere, plastic sphere or combination thereof.

In an embodiment of the invention, the oral dosage forms may comprise two or more controlled release components that release the drug(s) such as CD, LD, an ester of LD or salts thereof at different rates. In this embodiment, the oral dosage forms contain at least two controlled release components differing in type, number, thickness and/or composition of first coating comprising the rate controlling material, the second coating comprising the muco-adhesive material and/or the third coating comprising the enteric material.

Examples of LD include but are not limited to levodopa, L-DOPA, L-3,4-dihydroxyphenylalanine, and (S)-2-amino-3-(3,4-dihydroxyphenyl)propanoic acid.

An example of a decarboxylase inhibitor includes, but is not limited to CD. Additional decarboxylase inhibitors include alpha methyldopa, benserazide (Ro4-4602), and alpha-difluoromethyl-DOPA (DFMD) or salts thereof. In a preferred embodiment, the decarboxylase inhibitor is carbidopa.

An example of an ester of LD is a levodopa ethyl ester (LDEE; ethyl (2S)-2-amino-3-(3,4-dihydroxyphenyl)propanoate; CAS Number: 37178-37-3) and having the structure:

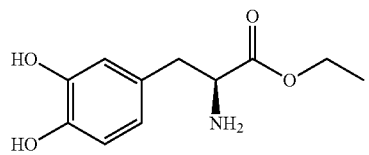 [SMILES: CCOC(=O)[C@@H](N)Cc1ccc(O)c(O)c1]

(levodopa ethyl ester; CAS Number 37178-37-3).

Additional examples of esters of LD include, but are not limited to:
levodopa butyl ester (butyl (2S)-2-amino-3-(3,4-dihydroxyphenyl)propanoate; CAS Number: 39638-52-3) having the structure:

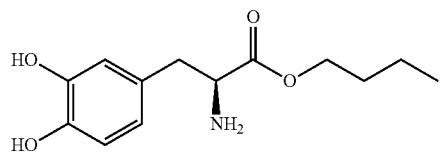 [SMILES: CCCCOC(=O)[C@@H](N)Cc1ccc(O)c(O)c1]

levodopa propyl ester; levodopa propyl ester (propyl (2S)-2-amino-3-(3,4-dihydroxyphenyl)propanoate; CAS Number: 39638-51-2) having the structure:

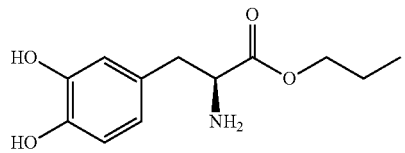 [SMILES: CCCOC(=O)[C@@H](N)Cc1ccc(O)c(O)c1]

and levodopa methyl ester (methyl (2S)-2-amino-3-(3,4-dihydroxyphenyl)propanoate; CAS Number: 7101-51-1), having the structure:

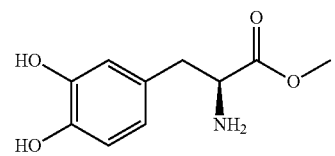

The ester of LD may be a salt, including, for example, a hydrated salt. The salt of LD esters may comprise an organic or inorganic acid addition salt such as an octonoate salt, myristate salt, succinate salt, succinate dihydrate salt, fumarate salt, fumarate dihydrate salt, mesylate salt, tartrate salt, sulfate salt, alkyl sulfate salt, maleate salt, citrate salt, phosphate salt, acetate salt, lactate salt, nitrate salt, hydrochloride salt, hydrobromide salt, hydroidioide salt or combination thereof.

For example, the succinate salt of an ester of LD or the succinate dihydrate salt may be a levodopa ethyl ester succinate (LDEE-S) or levodopa ethyl ester succinate dihydrate (LDEE-S-dihydrate or LDEE-S(d)).

As used herein, "levodopa equivalence" or "LD equivalence" means that amount of levodopa ester or salts thereof that contain equivalent amounts of levodopa, based on weight equivalence. For example, based on the molecular weights, 306 mg of levodopa ethyl ester succinate-dihydrate (LDEE-S-dihydrate) is equivalent to 228 mg of levodopa ethyl ester (LDEE) and to 200 mg levodopa (LD).

The muco-adhesive material employed in the present invention may be a homogenous muco-adhesive material, i.e., a single type of muco-adhesive material or polymer, or may comprise multiple types of muco-adhesive materials and/or polymers. The muco-adhesive material or polymer may possess certain characteristics such as being hydrophilic, hydrophobic, cationic, anionic and/or biocompatible and include multiple hydrogen bonding groups, hydrophobic surfaces, positively charged groups and/or negatively charged groups for adhesion to a mucosal surface so that the controlled release component can be held, prolonged or slowed at the site of absorption, thereby allowing the release of the LD or ester of LD from the controlled release component at the desired absorption site and thereby increase bioavailability. Further, the muco-adhesive material or polymer may be natural, synthetic or from a biological source. Further still, the muco-adhesive material or polymer may be composed of a single polymer or a combination of two or more different polymers. In one embodiment, the polymers may range in size from 10,000 daltons to 1,000,000 daltons and more preferably 20,000 daltons to 200,000 daltons.

An example of a muco-adhesive polymer includes, but is not limited to, a basic methacrylate copolymer, such as an amino methacrylate copolymer. A preferred example of a methacrylate copolymer is a basic butylated methacrylate copolymer, an amino methacrylate copolymer, or aminoalkyl methacrylate copolymer, such as Eudragit® E100 (poly (butyl methacrylate-co-(2-dimethylaminoethyl) methacrylate-co-methyl methacrylate) 1:2:1; CAS number: 24938-16-7; Evonik Industries). EUDRAGIT® E100 is a cationic copolymer based on dimethylaminoethyl methacrylate, butyl methacrylate, and methyl methacrylate with a ratio of 2:1:1 with the following monomer

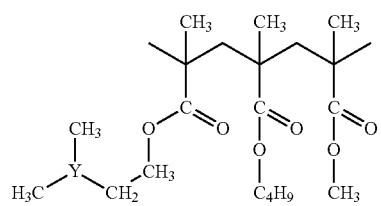

wherein Y is nitrogen. In a preferred embodiment, the average molar weight of EUDRAGIT® E100 is approximately 150,000 g/mol.

Other examples of muco-adhesive materials or polymers include, but are not limited to, a glyceride, steroidal detergent, polycarbophil (CAS Number 9003-97-8; Noveon® AA-1; Lubrizol Corp.), carbomer, cellulosics, chitosan

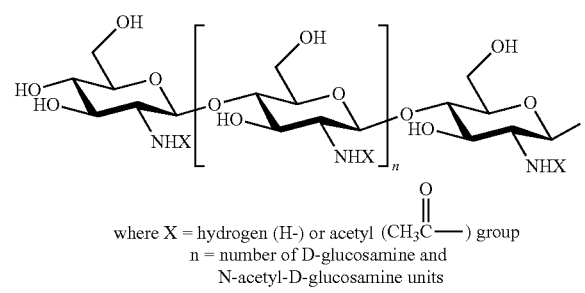

where X = hydrogen (H-) or acetyl (CH₃C—) group
n = number of D-glucosamine and N-acetyl-D-glucosamine units (CAS Number: 9012-76-4; Chitopharm® S with molecular weight range of 50,000 to 1,000,000 daltons), diethylaminodextran, diethylaminoethyldextran, polygalactosamine, polylysine, polyornithine, prolamine, polyimine, hyaluronic acid, sodium alginate, hydroxypropylcellulose (HPC), hydroxypropylmethylcellulose (HPMC), sodium carboxymethylcellulose (sodium CMC) and alginate (CAS Number: 9005-32-7) or combination thereof. Alginate is a homopolymer or heteropolymer composed of β-D-mannuronate (M) monomers, α-L-guluronate (G) monomers, or mixture of β-D-mannuronate and α-L-guluronate monomers

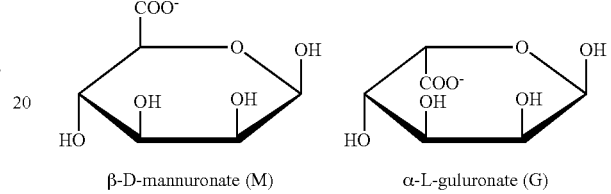

β-D-mannuronate (M)      α-L-guluronate (G)

linked through (1→4) or (1,4)-glycosidic bonds. The (1,4)-glycosidic linkages present in alginates are: β-D-mannuronate-(1,4)-β-D-mannuronate (MM), β-D-mannuronate-(1,4)-α-L-guluronate (MG), α-L-guluronate-(1,4)-β-D-mannuronate (GM) and α-L-guluronate-(1,4)-α-L-guluronate (GG), as can be seen below:

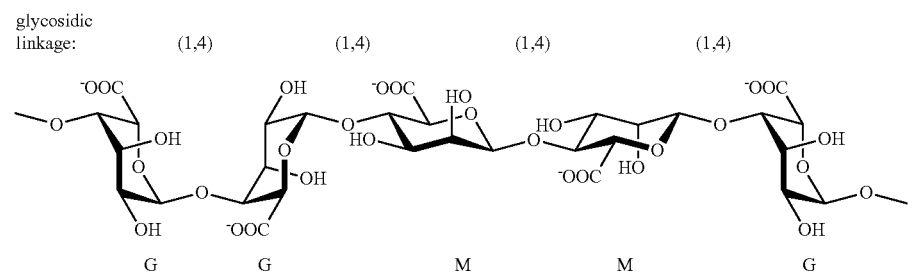

An alginate may be in the form of a polyanion or in the form of an acid, such as alginic acid. Further, alginate may be in the form of a salt of alginic acid, such as sodium alginate, potassium alginate, ammonium alginate, triethanolamine alginate, magnesium alginate or calcium alginate. Alternatively, alginate may be in the form of an ester of alginic acid such as propylene glycol alginate.

The muco-adhesive material or polymer may constitute about 1-75% of the mass of the controlled release component, preferably about 2-70% of the mass of the controlled release component, most preferably about 3-50% of the mass of the controlled release component. Preferably, the muco-adhesive material or polymer is Eudragit® E 100 alone or combined with at least one additional muco-adhesive material. The muco-adhesive material or polymer percentages of mass stated above are based on a multiparticulate with a bead size between 0.8 to 1.2 mm. If the bead size is larger or smaller than 0.8 to 1.2 mm, the skilled artisan will understand that the mass percentage described above should be adjusted accordingly.

Alternatively, the muco-adhesive material or polymer is a material capable of forming a positive ionic charge at the pHs present in the human gastro-intestinal tract. It is believed that the positive charge may allow the mucoadhesive material to interact with the negative charge of the intestinal walls and thereby slow or delay the gastrointestinal transit time of the controlled release component.

Enteric coating materials or polymers are known in the art. In general, enteric coating polymers are designed to prevent drug release from an oral solid dosage form in the low pH environment of the stomach, thereby delaying drug release until the dosage form reaches the small intestine. As such, the controlled release components of the invention have an in vitro release profile with minimal release of the active agent at pH 1.0. In the controlled release formulations of the invention, it is believed the third or outer enteric coating layer provides an additional advantage in preventing agglomeration of the controlled release components. That is, the enteric coat layer prevents the controlled release mucoadhesive components from sticking together in the low pH environment of the stomach.

The preferred enteric materials are shellac (esters of aleurtic acid), zein, cellulose acetate phthalate (CAP), poly (methacrylic acid-co-methyl methacrylate), poly(methacrylic acid-co-ethyl methacrylate), cellulose acetate trimellitate (CAT), poly(vinyl acetate phthalate) (PVAP), hydroxypropyl methylcellulose phthalate (HPMCP) and hydroxypropyl methylcellulose acetate succinates. The preferred enteric polymers release at a pH of greater than or equal to pH 5.5. Examples include Eudragit® L100 or Eudragit® L100-55. The enteric polymers may constitute about 1-40% of the mass of the controlled release component, preferably about 1.5-30%, most preferably about 1.5-25%. The enteric-coated polymer percentages stated above are based on a multiparticulate bead size between 0.8-1.2 mm. If the bead size is smaller or larger, the skilled artisan will understand that the mass percentage described above should be adjusted accordingly.

The third or outer enteric coating should be designed to dissolve at a pH greater than 5.0, at a pH of 5.5 or higher, at a pH of 6.0 or higher or a pH of 6.5 or higher. In certain embodiments, the third or outer enteric coating should be designed to dissolve at a pH in the range of 5.0 to 6.4, preferably in the range of 5.0 to 6.0.

The enteric coating polymer may comprise a methacrylic acid copolymer or multiple types of methacrylic acid copolymers. The methacrylic copolymer may comprise any of Eudragit® L 30 D-55

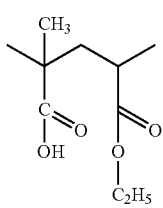

(poly(methacrylic acid-co-ethyl acrylate) 1:1; CAS Number 25212-88-8; Evonik Industries), Eudragit® L 100-55

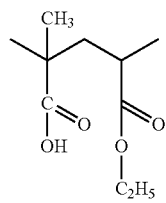

(poly(methacrylic acid-co-ethyl acrylate) 1:1; CAS Number 25212-88-8; Evonik Industries), Eudragit® L 100

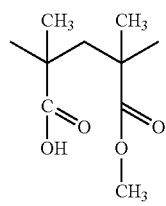

(poly(methacrylic acid-co-methyl methacrylate) 1:1; CAS Number 25086-15-1; Evonik 15 Industries), Eudragit® L 12.5

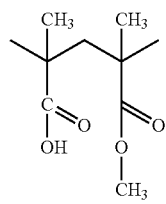

(poly(methacrylic acid-co-methyl methacrylate) 1:1; CAS Number 25086-15-1; Evonik Industries); Eudragit® S 100

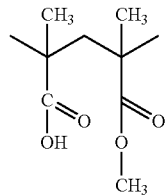

(poly(methacrylic acid-co-methyl methacrylate) 1:2; CAS Number 25086-15-1; Evonik Industries), Eudragit® S 12.5

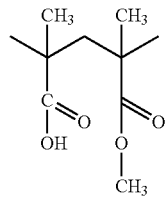

(poly(methacrylic acid-co-methyl methacrylate) 1:2; CAS Number 25086-15-1; Evonik Industries), and Eudragit® FS 30 D

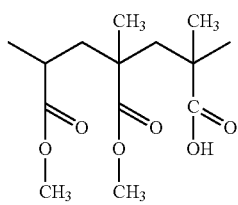

(poly(methyl acrylate-co-methyl methacrylate-co-methacrylic acid) 7:3:1; CAS Number 26936-24-3; Evonik Industries) or a combination thereof.

In a preferred embodiment of present invention, the controlled release component comprises a first rate controlling coating over the drug-containing core (i.e. applied to or surrounding the drug containing core with or without a seal coating), a second coating comprising a muco-adhesive material that is applied to or surrounding the rate controlling coating (with or without a seal coating) and a third coating comprising an enteric material that is applied to or surrounding the second coating (with or without a seal coating). The first rate controlling coating may comprise a controlled release material or polymer such as ethylcellulose, cellulose acetate, Eudragit® E, Eudragit® RS, Eudragit® RL, and Eudragit® NE, or mixtures thereof. Preferably, the controlled release materials are not soluble in water at neutral pH. Additional the controlled release materials or polymers that may be used are described in U.S. Pat. No. 5,002,776 which is incorporated herein by reference. In certain embodiments the controlled release material or polymer is cellulose acetate, ethylcellulose or a mixture thereof. The first or rate controlling coating may further comprise a pore forming agent or a flux enhancer to adjust the release rate of the drug from the core. Preferably, the pore forming agent or flux enhancer is a water soluble material such as a salt, i.e., NaCl, KCl, a sugar, i.e., lactose, sucrose, mannitol, povidone, copovidone, polyethylene glycol, hydroxypropyl cellulose, hydroxypropyl methylcelluose or combinations thereof. If the pore forming agent or flux enhancer is a water soluble polymer, it should have a low molecular weight such as below 100,000, preferably below 50,000 and/or should rapidly dissolve in water, i.e., 2 wt % of the water soluble polymer should dissolve in 100 ml of water within 15 minutes or less, preferably 10 minutes or less, and most preferably 5 minutes or less at 25° C.

The controlled release component may also comprise a hydrophobic controlled release material in addition to or in place of the controlled release materials described above. Examples of hydrophobic materials that can be used include beeswax, white wax, emulsifying wax, hydrogenated vegetable oil, hydrogenated castor oil, microcrystalline wax, cetyl alcohol, stearyl alcohol, free wax acids such as stearic acid, esters of wax acids, propylene glycol monostearate, glycerol monostearate, carnauba wax, palm wax, candelilla wax, lignite wax, ozokerite, ceresin wax, lardaceine, China wax and mixtures thereof. Other possible controlled release excipients useful in the present invention include saturated hydrocarbons having from 25 to 31 carbon atoms, saturated alcohols having from 25 to 31 carbon atoms, saturated monocarboxylic acids having from 25 to 31 carbon atoms, esters obtained from said alcohols, and monocarboxylic acids which are described in U.S. Pat. No. 6,923,984, incorporated herein by reference.

In an alternate embodiment, the controlled release component comprises a matrix core comprising a mixture of a controlled release material, which may be the afore-described controlled release materials and/or hydrophobic materials and the drug, i.e., CD, LD and/or ester of LD or salts thereof and/or decarboxylase inhibitor. The matrix core may further comprise one or more pharmaceutically acceptable excipients such as lubricants, fillers, binders, disintegrants, glidants, surfactants (sometimes referred to as wetting agents), pH adjusting agents, antioxidants or mixtures of the foregoing. In this embodiment, the matrix core may be further coated with a rate controlling coating or polymer before being coated with the muco-adhesive coating and the outer enteric coating.

In another alternate embodiment, the controlled release component may incorporate a controlled release material, which may be the afore-described controlled release materials and/or hydrophobic material, into the muco-adhesive coating. The muco-adhesive material may also function as the controlled release material or contribute to the controlled release of the drug form the controlled release component.

The controlled release material may constitute about 1-35% of the mass of the controlled release component, preferably about 2-30% and most preferably about 3-25%.

The muco-adhesive coating or layer and enteric coating or layer employed in the present invention may further comprise one or more pharmaceutically acceptable excipients such as plasticizers, lubricants, fillers, binders, disintegrants, glidants, surfactants (sometimes referred to as wetting agents), pH adjusting agents, antioxidants, or mixtures of the foregoing in addition to the muco-adhesive material and enteric material.

Some commonly known plasticizers include adipate, azelate, enzoate, citrate, stearate, isoebucate, sebacate, triethyl citrate, tri-n-butyl citrate, acetyl tri-n-butyl citrate, citric acid esters, and those described in the *Encyclopedia of Polymer Science and Technology*, Vol. 10 (1969), published by John Wiley & Sons. The preferred plasticizers are triacetin, acetylated monoglyceride, grape seed oil, olive oil, sesame oil, acetyltributylcitrate, acetyltriethylcitrate, glycerin sorbitol, diethyloxalate, diethylmalate, diethylfumarate, dibutylsuccinate, diethylmalonate, dioctylphthalate, dibutylsebacate, triethylcitrate, tributylcitrate, glyceroltributyrate and combinations thereof. Depending on the particular plasticizer, amounts from about 0% to about 25%, and preferably about 2% to about 15%, of the plasticizer can be used based upon the total weight of the controlled release, muco-adhesive and/or enteric coating.

Lubricants useful in pharmaceutical formulations are known in the art. Examples of a suitable lubricant include, but are not limited to, stearic acid, lauric acid, myristic acid, palmitic acid, fatty acid, magnesium stearate, calcium stearate, zinc stearate, sodium stearate, Stear-O-Wet®, sodium stearyl fumarate, salt of a fatty acid, metallic salt of fatty acid, glyceryl monostearate, glyceryl tribehenate, glyceryl dibehenate, Compritol® 888 ATO, glyceride ester, sorbitan monostearate, sucrose monopalmitate, sugar ester, fatty acid ester, talc, hydrated magnesium silicate, PEG 4000, boric acid, Carbowax (PEG) 4000/6000, sodium oleate, sodium benzoate, sodium acetate, sodium lauryl sulfate, magnesium lauryl sulfate, Sterotex, wax, or mixture thereof.

Examples of fillers that may be employed in the composition of the present invention include sugars, such as lactose, sucrose, mannitiol, dibasic calcium phosphate, microcrystalline cellulose, calcium carbonate, magnesium carbonate, calcium sulfate, powdered cellulose, silicified microcrystalline cellulose, magnesium carbonate, magnesium oxide, starch, and mixtures thereof. The filler may constitute about 1-50% of the mass of the controlled release component, preferably about 2-45% and most preferably about 5-40%. Similarly, the filler may constitute about 1-50% of the mass of the immediate release component, preferably about 2-45% and most preferably about 5-40%.

Examples of binders that may be employed in the compositions of the present invention include acacia, povidone, hypromellose, hydroxypropyl cellulose, hydroxyethyl cellulose, polyethylene oxide, polymethacrylates, methyl cellulose, ethyl cellulose, pregelatinized starch, gelatin, tragacanth, zein, or mixtures thereof. Preferably, the binder is selected from povidone, hypromellose, hydroxypropyl cellulose, hydroxyethyl cellulose, polymethacrylates, methyl cellulose, gelatin and ethyl cellulose, or mixtures thereof. Especially preferred binders include water soluble binders such as povidone, hypromellose, hydroxypropyl cellulose, gelatin and mixtures thereof. The binder may constitute about 0.1-15% of the mass of the controlled release component, preferably about 0.2-10% and most preferably about 0.5-5%. The binder may constitute about 0.1-15% of the mass of the immediate release component, preferably about 0.2-10% and most preferably about 0.5-5%.

Examples of disintegrants that may be employed in the compositions of the present invention include croscarmellose sodium, starch, crospovidone, sodium starch glycolate, alginic acid, calcium carboxymethylcellulose, sodium carboxymethylcellulose, calcium carboxymethylcellulose, powdered cellulose, chitosan, guar gum, magnesium aluminium silicate, methylcellulose, sodium alginate, and mixtures thereof. The disintegrant may constitute about 0.1-15% of the mass of the immediate release component, preferably about 0.2-10% and most preferably about 0.5-5%.

Examples of glidants that may be employed in the compositions of the present invention include colloidal silicon dioxide, cornstarch, talc or mixtures thereof.

One or more surfactants may also be employed in the compositions of the present invention. The surfactant may be a non-ionic surfactant or an ionic surfactant. Examples of non-ionic surfactants include polyethoxylated castor oil, a polyoxyethylene alkyl ester, a polyglycolyzed glyceride, a sorbitan fatty acid ester, a glycerin fatty acid ester, a fatty acid polyglyceride, a fatty acid alcohol polyglycol ether, acetylene glycol, acetylene alcohol, an oxyalkylene block polymer, a polyoxyethylene alkyl ether, a polyoxyethylene alkylaryl ether, a polyoxyethylene styrylaryl ether, a polyoxyethylene glycol alkyl ether, a polyoxyethylene fatty acid ester, a polyoxyethylene sorbitan fatty acid ester, a polyoxyethylene glycerin fatty acid ester, a polyoxyethylene hydrogenated castor oil, a polyoxypropylene fatty acid ester, or a mixture of the foregoing. A further listing of possible non-ionic surfactants can be found on pages 1243-1249 of Martindale, The Extra Pharmacopoeia $29^{th}$ ed. which is incorporated herein by reference.

In certain embodiments, the non-ionic surfactants may comprise fatty alcohol acid or amide ethoxylates, monoglyceride ethoxylates, sorbitan ester ethoxylates alkyl polyglycosides, mixtures thereof, and the like. Certain non-ionic surfactants include polyoxyethylene derivatives of polyol esters, such as Polysorbate 20 (TWEEN 20®), Polysorbate 40 (TWEEN 40®) Polysorbate 60 (TWEEN 60®), and Polysorbate 80 (TWEEN 80®).

In certain embodiments, the non-ionic surfactant may also comprise d-alpha tocopheryl polyethylene glycol 1000 succinate (TPGS), nonoxinols, poloxamers, sorbitan monolaurate, sorbitan monooleate, sorbitan monopalmitate, sorbitan monostearate, sorbitan sesquioleate, sorbitan trioleate, tyloxapol, and mixtures of the foregoing.

Any variety of ionic surfactants may also be incorporated into the compositions of the present invention. Suitable ionic surfactants include, but are not limited to, carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, phosphates, quaternary ammonium salts, and ethoxylated amines. An example of a preferred ionic surfactant is sodium lauryl sulfate.

The surfactant may constitute about 0.1-15% of the mass of the controlled release component or the immediate release component, preferably about 0.2-10% and most preferably about 0.5-5%.

Examples of pH adjusting agents that may be employed in the compositions of the present invention include pharmaceutically acceptable acids or bases which may be present to adjust the pH of intermediate compositions leading up to the final compositions and to adjust the pH of the drug environment of final compositions to a desired or optimum pH range. Representative examples of pharmaceutically acceptable acids that may be used include, but are not limited to, acetic acid, citric acid, fumaric acid, hydrochloric acid, malic acid, nitric acid, phosphoric acid, propionic acid, sulfuric acid, tartaric acid, and mixtures thereof. Representative examples of pharmaceutically acceptable bases that may be used include but are not limited to ammonia, ammonium carbonate, diethanolamine, potassium hydroxide, sodium bicarbonate, sodium carbonate, sodium hydroxide, trolamine, and mixtures thereof. In certain embodiments the pH adjusting agent is an acid, preferably an organic acid and will constitute about 0.5-20% of the mass of the controlled release component, preferably about 0.75-15% and most preferably about 1-10%. Alternatively, the pH adjusting agent is an acid, preferably an organic acid and will be present in the controlled release component in a molar ratio of acid to levodopa of about 1:4 to about 4:1, preferably about 1:3 to about 3:1 and most preferably about 1:2 to about 2:1. Certain embodiments of the present invention, the immediate release components, the controlled release components and/or the final oral dosage forms are free or substantially free of a pH adjusting acid, preferably a pH adjusting organic acid and most preferably a pH adjusting carboxylic acid such as acetic acid, citric acid, fumaric acid, malic acid, propionic acid, tartaric acid, and mixtures thereof.

Examples of antioxidants that may be employed in the compositions of the present invention include ascorbic acid, ascorbyl palmitate, butylated hydroxyanisole, butylated hydroxytoluene, hypophosphorous acid, monothioglycerol, potassium metabisulfate, propyl gallate, sodium bisulfite, sodium formaldehyde sulfoxylate, sodium metabisulfate, sodium sulfate, sodium thiosulfate, sodium dioxide, tocopherol, and mixtures thereof.

In an embodiment of the invention, the CD and the LD or LD equivalence are present in the dosage form of the invention in a weight ratio of about 1:1 to about 1:10, preferably about 1:3 to about 1:5 and most preferably about 1:4. Certain embodiments comprise CD and LD in a ratio of about 1:4 and wherein all or substantially all of the CD is in the immediate release component.

Examples of useful amounts of LD or LD equivalence to CD include: (a) 200 mg:31.25 mg; (b) 200 mg:50 mg; (c) 255.6 mg:50 mg; (d) 360 mg:50 mg; (e) 95 mg:23.75 mg; (f) 145 mg:36.25 mg; (g) 195 mg:48.75 mg; (h) 245 mg:61.25 mg; or (i) 390 mg:97.5 mg; with each value capable of varying by ±10%. Further examples include amounts of LD:CD or LD equivalence:CD as follows: (a) 95 mg:23.75 mg; (b) 145 mg:36.25 mg; (c) 195 mg:48.75 mg; or (d) 245 mg:61.25 mg; with each value capable of varying by ±10%. Additional examples of the present invention include dosage forms, comprising: (a) about 140 mg LD and about 35 mg of CD; (b) about 210 mg LD and about 52.5 mg of CD; (c) about 280 mg LD and about 70 mg of CD; and (d) about 350 mg LD and about 87.5 mg of CD. The foregoing values are based on the weight of anhydrous CD. If a monohydrate form of CD is employed the amounts will be slightly higher. For example 35 mg of anhydrous CD is equivalent to 37.79 mg of CD monohydrate; similarly 70 mg of anhydrous CD is equivalent to 75.58 mg of CD monohydrate.

In an embodiment of the invention, the immediate release component may comprise less LD or LD equivalence than the controlled release component. For example, the ratio of LD or LD equivalence in the immediate release component to that in the controlled release component can be in the range of 0.15 to 0.49. For example, a ratio in weight of LD or LD equivalence in the controlled release component: immediate release component is at least about 2:1, most preferably 3:1. Preferably the amount of LD or LD equivalence in the immediate release component should provide a therapeutic dose of LD within one hour or less after administration of the dosage form, preferably within 45 minutes or less after administration and most preferably about 30 minutes or less after administration.

As discussed above, in certain embodiments comprising a decarboxylase inhibitor such as CD, all or substantially all of decarboxylase inhibitor should be in the immediate release component. The amount of immediate release decarboxylase inhibitor, preferably CD, in the immediate release component(s) should range from about 75% to about 100% based on the total amount of decarboxylase inhibitor in the oral dosage forms, preferably about 80% to 100%, and most preferably about 85%, 86%, 87%, 88%, 89%, 90%, 91%, 92%, 93%, 94%, 95%, 96%, 97%, 98%, 99 or 100%.

In one embodiment of the invention, the controlled release component comprise one or more, beads, pellets, tablets, mini-tablets or granules having a size that passes through 12, 14, or 16 mesh but may be retained on 18, 24 or 25 mesh screens. Further, the beads, pellets, tablets, mini-tablets or granules may have a size that passes through 14 mesh but may be retained on 18 or 24 mesh screens. In certain embodiments, the dosage forms of the invention comprise a plurality beads, pellets, tablets, mini-tablets or granules having a size that passes through 12, 14, or 16 mesh but may be retained on 18, 24 or 25 mesh screens.

The controlled release component will have an in vitro dissolution profile showing minimal release of the LD and/or ester of the LD or a salt thereof at pH 1.0 and extended release of the LD and/or ester of LD or a salt thereof near neutral pH, for example at or near pH 7. For example, minimal release may entail less than 20% release of LD, preferably less than 10%, most preferably less than 5% using United States Pharmacopeia (USP) I dissolution method at agitation speed of 75 rpm in Simulated Gastric Fluid (pH 1.0, without enzyme) for 2 hrs. Further, extended release may involve release at over at least four and up to an additional 8 hours at or near pH 7, upon changing to Simulated Intestinal Fluid (pH 7.0, without enzyme) after first 2 hrs in Simulated Gastric Fluid (pH 1.0, without enzyme) using USP I dissolution method at agitation speed of 75 rpm. Further still, as used here, at or near pH 7 includes a pH at or about pH 6.5, 6.6, 6.7, 6.8 6.9, 7.1, 7.2, 7.3, 7.4, 7.5 or 7.6.

The oral dosage forms of the present invention should comprise one or more immediate release components and one or more controlled release components wherein following administration to a human patient the immediate release component(s) should provide a therapeutic dose of LD within one hour or less after administration of the dosage form, preferably within 45 minutes or less after administration and most preferably about 30 minutes or less after administration. After the therapeutic plasma level of LD is obtained by the immediate release component(s), the controlled release component(s) should provide and/or maintain a therapeutic plasma level of LD over a period of at least 4-12 hours, preferably 6-12 hours and most preferably 5, 6, 7, 8, 9, 10, 11 or 12 hours after administration. To obtain this therapeutic level, the controlled release component(s) should exhibit the following in vitro release profiles when tested using a USP Type I or II apparatus, at 37° C., with a rotational speed of 75 rpms and 900 ml of an aqueous media with a pH between 6.8-7.4 and preferably at a pH of 7:

| | LevodOpa Released | | |
|---|---|---|---|
| Time | Preferred | More Preferred | Most Preferred |
| 2 | 0-60% | 10-55% | 15-50% |
| 4 | 25-90% | 30-85% | 35-80% |
| 6 | 35-100% | 40-100% | 50-100% |

The amount of LD released in the above table is based on the total amount of LD or ester of LD or salt thereof present in the controlled release component(s). In certain embodiments the controlled release component(s) should also release less than 25% of the LD or ester of LD or salt thereof, preferably less than 20% and most preferably less than 15% when tested using a USP Type I or II apparatus, at 37° C., with a rotational speed of 75 rpms and 900 ml of an aqueous media with a pH of 1 for 2 hours.

In certain embodiments the oral dosage forms of the present invention comprises: (i) one or more immediate release components comprising LD and CD and (ii) one or more controlled release components, i.e., controlled release particles such as beads, pellets, tablets, mini-tablets, or granules comprising: (a) a core comprising LD, optionally CD and at least one pharmaceutically acceptable excipient, (b) a layer or coating surrounding the core comprising a muco-adhesive material and (c) an outer coating comprising an enteric material surrounding the muco-adhesive coating (b). This embodiment may also comprise a controlled release material in the core or a coating comprising a controlled release material surrounding the core and beneath the coating comprising the muco-adhesive material as well as cosmetic and/or non-functional seal coatings as previously described. When this embodiment of the dosage form of the present invention is tested using a USP Type I or Type II apparatus with 500-900 mL of an aqueous medium with a pH from about 1 to about 7.5, about 75% to 100% of the CD is released within 30 minutes, preferably about 85% to 100% of the CD is released within 30 minutes and most preferably about 90% to 100% of the CD is released within 30 minutes. In addition, when this embodiment of the dosage form is tested using a USP Type I or Type II apparatus and 500-900 mL of an aqueous medium with a pH from about 1 to about 4.0, about 15% to 45% of the LD is released within 30 minutes, preferably about 20% to 40% of the LD is released within 30 minutes and most preferably about 25% to 35% of the LD is released within 30 minutes. When this embodiment of the dosage form is tested using a USP Type I apparatus, at 37° C.±0.5° C., with a rotational speed of 75 rpms and 500-900 ml of simulated gastric fluid for 2 hours and pH 6.8 phosphate buffer thereafter the following LD in vitro profile is exhibited:

| | Levodopa Released | | |
|---|---|---|---|
| Time (hour) | Preferred | More Preferred | Most Preferred |
| 2 | 20-60% | 25-55% | 30-50% |
| 3 | 40-80% | 45-75% | 50-75% |
| 4 | 60-100% | 65-100% | 70-100% |
| 7 hours | NLT 80% | NLT 85% | NLT 90% |

NLT = Not Less Than.

In a further embodiment, the present invention comprises: a) one or more immediate release components as previously described; b) one or more controlled release components as previously described and c) one or more enteric coated components. The enteric coated component comprises a core comprising LD or ester of LD or salt thereof and/or a decarboxylase inhibitor and at least one pharmaceutically acceptable excipient as previously described and an enteric coating. The enteric coated component will release 100% of the LD or ester of LD or salt thereof and/or a decarboxylase inhibitor within 90 minutes, preferably 60 minutes and most preferably within 45 minutes when tested using a USP Type I or II apparatus, at 37° C., with a rotational speed of 75 rpms and 900 ml of an aqueous media with a pH between 6.8-7.4, preferably at pH 7. The enteric coated component will also release less than 25% of the LD or ester of LD or salt, preferably less than 20% and most preferably less than 15% when tested using a USP Type I or II apparatus, at 37° C., with a rotational speed of 75 rpms and 900 ml of an aqueous media with a pH of 1.

The LD and/or ester of LD or a salt thereof released from the controlled release component(s) may produce an in vivo LD a plasma profile (e.g., mean in vivo LD plasma profile) comprising a peak occurring not before about two hours after administration to a subject and provides at least three hour duration for LD plasma concentration above 50% the maximum value of the peak concentration ($C_{max}$). In another embodiment, in the plasma profile, the peak occurs after about one and a half hours after administration to the subject and exhibits at least a four-hour duration for LD plasma concentration at or above 50% of $C_{max}$. By way of example, the profile may be achieved under fasting conditions.

When the formulation of the invention comprises an immediate release component and a controlled release component, the in vivo LD plasma profile following oral administration of the dosage form of the present invention to a subject may comprise a time of administration of an oral dosage form; an LD plasma concentration corresponding to $C_{max}$ occurring within about 6 hours or 7 hours after administration of the dosage form; a mean time to reach 50% of $C_{max}$ within one hour of administration, more preferably within 30 minutes. The time to 50% of $C_{max}$ is less than one hour and 50% of $C_{max}$ is maintained for at least 5.0 hours. The time after administration of the dosage form when the maximum plasma concentration is reached ($T_{max}$) is between 30 minutes and 7 hours. Preferably, the LD plasma level is maintained at or above 50% of $C_{max}$ for at least 5.5 hours, more preferably, for at least 6.0 hours, even more preferably, for at least 6.5 hours, and most preferably for at least 7.0 hours.

It is understood by those skilled in the art that the pharmacokinetic parameters recited herein may be obtained by single or multidose dose studies to healthy subjects or PD patients unless specifically stated. It is also understood that the pharmacokinetic parameters recited herein may be obtained under fed or fasting conditions. It is further understood that the pharmacokinetic parameters recited herein are mean values, unless specifically stated, obtained from single or multidose studies employing at least 3 or more subjects or patients.

In one embodiment, the dosage forms of the invention may have a ratio of said $C_{max}$ to the mass of LD or LD equivalence. The concentration may be measured in units of ng/mL, to the mass of LD or LD equivalence in the formulation, where said mass is measured in mg, of between 2:1 and 6:1. The ratio may be between 2.5:1 and 5.5:1, preferably, greater than or equal to about 3:1.

The combination of immediate release components and controlled release components of the invention provide the near infusion-like profile as evident from the plateau in the LD plasma profile (see, e.g., FIG. 5). The LD $C_{max}$ itself is not clinically relevant. What is clinically relevant is the time to reach a therapeutic level of LD (e.g., an LD level of 50% $C_{max}$) and the time maintained at or above the therapeutic level (e.g., 50% $C_{max}$). The short time to reach a therapeutic LD level is associated with a faster "on" time for PD patients, whereas the prolonged period at or above therapeutic levels provides the desired steady "infusion-like" profile.

It is an advantage of the present invention to provide a sustained LD plasma concentration for a duration greater than 5 hrs and a more consistent duration with percent coefficient of variation (CV) of mean duration of LD plasma concentrations >50% $C_{max}$ of less than 35%, preferably less than 30%.

The skilled artisan will appreciate that daily dosages having an amount of active agent sufficient or effective to treat diseases associated with reduced or impaired dopamine levels may generally contain from about 25 mg to about 6000 mg of LD or LD equivalence dose in combination with from about 5 mg to about 1500 mg of CD.

Dosage forms of the present invention may contain 25-750 mg of LD or LD equivalence, preferably about 50-500 mg and most preferably about 80-400 mg wherein 25% to 50% of the total LD or LD equivalence is in the immediate release component, preferably 25% to 40% and most preferably 25% to 35%. Further, dosage forms of the present invention may contain CD ranging from 25-300 mg, preferably 25-200 mg and most preferably 30-150 mg wherein all or substantially all of the CD is in the immediate release component.

By way of example, the total daily dose of LD from the dosage forms of the invention may be less than about 2500 mg. For example, the total daily LD dose may be between 800 mg to 2500 mg. In a further example, the total daily LD dose may be about 855 mg, 1140 mg, 1170 mg, 1305 mg, 1755 mg, 2205 mg, or 2340 mg. In another embodiment, the total daily CD dose may be about 100 mg to 800 mg. The total daily dose will depend upon the patient's individual characteristics such as age, sex, weight and severity of PD symptoms.

The dosing frequency may also vary, depending on the need of the subject. For example, the dosing frequency of the formulations of the invention may be two, three, four or five times a day preferably two or three times a day. In another example, the dosing frequency may be a maximum of five times a day.

Actual dosage levels of active ingredient in the compositions of the present invention may be varied so as to obtain an amount of active ingredient that is effective to obtain a desired therapeutic response for a particular composition.

The formulations of the invention may be administered as a single dose, or may comprise of a number of smaller doses, such as two 100 mg dose of LD for a total 200 mg dose, to be administered or consumed within a short period of time, such as within 15 minutes or less, preferably within 10 minutes or less and most preferably within 5 minutes of less. It is understood that the precise dosage and duration of treatment is a function of the disease being treated and may be determined using known practices. It is to be noted that dosage values may also vary with the severity of the condition to be alleviated. It is to be further understood that for any particular subject, specific dosage regimens should be adjusted over time according to the individual need and the professional judgment of the person administering or supervising the administration of the formulations of the invention, and that the concentration ranges set forth herein are exemplary only and are not intended to limit the scope or practice of the claimed compositions. Preferably the doses may be administered 2, 3 or 4 times a day (per 24 hour time period), and most preferably 2 or 3 times a day.

The LD bioavailability of the dosage forms of the present invention compared to an immediate release CD-LD product should be at least 70%, 75%, 80%, 85%, 90% or more.

Optimally, after administration to a patient suffering from a condition associated with reduced or impaired dopamine levels, a dosage form of the invention releases LD into the plasma of the patient at a steady or near constant level without significant decrease or fluctuation for an extended amount of time, thereby reducing motor fluctuations.

Preferred compositions of the present invention include:

A multiparticulate formulation comprising: a) one or more immediate release component(s) comprising LD and/or CD and optionally at least one pharmaceutically acceptable excipient as previously described and b) one or more controlled release component(s) comprising controlled release beads, pellets, tablets, mini-tablets, or granules wherein the beads, pellets, tablets, mini-tablets, or granules comprise a core of LD free or substantially free of CD and at least one pharmaceutically acceptable excipient as previously described, a muco-adhesive coating or layer applied to and/or surrounding the core and an enteric coating surrounding the muco-adhesive coating or layer wherein the controlled release beads, pellets, tablets, mini-tablets, or granules also comprises a controlled release material. The controlled release material may be: i) mixed with the LD to form a controlled release matrix core, ii) applied as a coating or layer onto the core comprising the LD and at least one pharmaceutically acceptable excipient; iii) incorporated or mixed into the muco-adhesive coating or layer or iv) a combination of (i), (ii) and/or (iii). Cosmetic and/or seal coatings as previously described may also employed in immediate release and controlled release components of this embodiment.

An alternative preferred compositions includes:

A multiparticulate formulation comprising: a) one or more immediate release component(s) comprising of LD, CD and optionally at least one pharmaceutically acceptable excipient as previously described; b) one or more controlled release component(s) free or substantially free of CD comprising beads, pellets, mini-tablets or granules wherein the beads, pellets, tablets, mini-tablets or granules comprise a core of LD and at least one pharmaceutically acceptable excipient as previously described, a muco-adhesive coating or layer applied to and/or surrounding the core and an enteric coating surrounding the muco-adhesive coating or layer wherein the controlled release beads, pellets, tablets, mini-tablets or granules also comprises a controlled release material and c) an enteric coated component comprising a plurality of enteric coated beads, pellets, mini-tablets or granules comprising a core comprising LD and/or a decarboxylase inhibitor and at least one pharmaceutically acceptable excipient as previously described and an enteric coating surrounding the core. The controlled release material employed in the controlled release component may be: i) mixed with the LD and at least one pharmaceutically acceptable excipient to form a controlled release matrix core, ii) applied as a coating or layer onto the core of the LD and at least one pharmaceutically acceptable excipient; iii) incorporated or mixed into the muco-adhesive coating or layer or iv) a combination of (i), (ii) and/or (iii). The enteric coated component will release 100% of the LD and/or a decarboxylase inhibitor within 90 minutes, preferably 60 minutes and most preferably within 45% when tested using a USP Type I or II apparatus, at 37° C., with a rotational speed of 75 rpms and 900 ml of an aqueous media with a pH between 6.8-7.4. Cosmetic and/or seal coatings as previously described may also employed in immediate release and controlled release components of this embodiment.

EXAMPLES

Example 1

I. Development of LDEE-S Beads for IPX203-B-12-01
Development of Core LDEE-S Breads
Preparation of Core Beads Required amounts of LDEE-S-Dihydrate, Microcrystalline Cellulose, Fumaric acid, Povidone K29-32, ethanol and Purified Water were dispensed. The alcohol and the purified water were charged into a container and stirred using a stir bar. Povidone was slowly added into the ethanol/water mixed solvent. Mixing continued until the Povidone was completely dissolved, and the spray pump was calibrated to the target granulation spray rate.

LDEE-S-Dihydrate, Microcrystalline Cellulose, Fumaric acid, and Povidone were charged into a high shear granulator and dry mixed for 1-5 minutes at impeller speed of 75 rpm and chopper speed of 1000 rpm. The Povidone solution was sprayed into the granulation bowl and granulation continued with either ethanol or water as necessary. The granules were wet mixed for 2 minutes, after the spraying was completed.

The wet granules were extruded using the extruder (MG 55 Multi Granulator) equipped with a 0.8 mm hole size screen at extruder speed of 55 rpm. the extrudates were collected into double polyethylene lined bags. The collected extrudate was weighed and adjusted in the quantities ranging from 170-210 g per load.

One load of the weighed extrudate was charge into a spheronizer equipped with a 3 mm cross hatch disc. The extrudate was spheronized at a spheronisation speed of 1400 rpm for 1-10 mins. The spheronized beads were discharge into double polyethylene bags. The remaining extrudate were spheronized until all the double polyethylene-lined bags are completed.

The wet beads were dried in a fluid bed drier (Glatt GPCP-1) at an Inlet temperature of 35±10° C. until Loss on Drying was not more than 5.0%. The steps above were repeated until additional sub loads had been processed.

The dried beads were passed through a mechanical sieve (Vibroscreen) equipped with a 24-MG mesh screen at the bottom, 18-MG mesh screen in the middle, and 16-MG mesh screen at the top. The beads that remained on 18-US mesh and 24-MG mesh screens were collected into double polyethylene lined bags.

Muco-Adhesive/Rate-Controlling Sub-Layer Coating

The batch yield was determined. The required amounts of Amino Methacrylate Copolymer (Eudragit® E100) and Talc were calculated and dispensed. Purified Water, Acetone and Isopropyl Alcohol were dispensed into a stainless steel container and stirred using stir bar. While stirring, Amino Methacrylate Copolymer (Eudragit® E100) was slowly added into the vortex of the mixed solvent. Mixing continued until the copolymer completely dissolved. While stirring, Talc was slowly disperse into the vortex of the solution. Mixing continued until the material was completely dispersed. The suspension was continually stirred throughout the coating process.

The spray pump was calibrated to the target coating spray rate of the peristaltic pump using the suspension solution above. The core beads were coated using Glatt GPCG 1 equipped with a Wurster insert at Inlet air temperature of 35±10° C., Atomization air pressure of 1.0-2.0 bars and Wurster partition height of 15-30 mm. During coating, the inlet air temperature, exhaust flap, and spray rate were adjusted to maintain the exhaust air temperature between 30±5° C.

After the target amount of coating solution was sprayed, the coated beads were dried at an inlet air temperature of 40±10° C. for 90 minutes. The dried beads were passed through a mechanical sieve (Vibroscreen) equipped with a pan at the bottom, 14-MG mesh screen in the middle, and 12-MG mesh screen at the top. The beads that remained in the pan and 14-MG mesh screens were collected into double polyethylene lined bags.

Enteric Coating

The batch yield was determined. Based on the batch yield, the required amounts of Triethyl Citrate, Talc and an enteric copolymer, either Methacrylic Acid Copolymer, Type A, (Eudragit® L100)/Methacrylic Acid Copolymer, Type B, (Eudragit® S) at 1/2 weight ratio for IPX203-C0006 or Eudragit® LI00-55 for IPX203-C0004 and IPX203-C0005 were calculated and dispensed. Acetone and Isopropyl Alcohol for IPX203-C0006 or Acetone, Isopropyl Alcohol and purified water for IPX203-C0004 and IPX203-C0005 were dispensed into a stainless steel container and stirred using stir bar. While stirring, the enteric copolymer and Triethyl Citrate were added slowly into the vortex of the mixed solvent. Mixing continued until the copolymer was completely dissolved.

While stirring, Talc was added slowly into the vortex of the solution. Mixing continued until the material was completely dispersed. The suspension was continually stirred throughout the coating process. The spray pump was calibrated to the target coating spray rate of the peristaltic pump using the suspension solution.

Eudragit® E-coated beads were coated with the enteric composition using Glatt GPCG 1 equipped with a Wurster insert at Inlet air temperature of 35±10° C., Atomization air pressure of 1.0-2.0 bars and Wurster partition height of 15-30 mm. During coating, the inlet air temperature, exhaust flap, and spray rate were adjusted to maintain the exhaust air temperature between 30±5° C.

After the target amount of coating solution was sprayed, the enteric-coated beads were dried at an inlet air temperature of 40±10° C. for 120 minutes. The dried beads were passed through a mechanical sieve (Vibroscreen) equipped with a pan at the bottom, 14-MG mesh screen in the middle, and 12-MG mesh screen at the top. The beads that remained in the pan and 14-MG mesh screens were collected into double polyethylene lined bags.

Encapsulation

The batch yield was determined. Based on the batch yield, the required amounts of the enteric coated beads (also referred to herein as beads having an outer enteric coating polymer layer) and talc were calculated and dispensed. The Enteric Coated Beads and Talc were placed in an appropriated sized plastic bag and were manually blended by shaking the plastic bag with the beads and Talc for 10 minutes. The blend was encapsulated with 00 size gelatin capsules, using MG Flexalab Encapsulator at the target fill weight of 482 mg, 537 mg and 472 mg for IPX203-C0004, IPX203-C0005 and IPX203-C0006 respectively, so that the target LDEE dose/2 capsules was 228 mg, equivalent to LD dose of 200 mg.

Rationale for Components and Coatings in Formulation

The core bead formulation was developed utilizing microcrystalline cellulose (MCC) as filler since the wetted MCC has the desired rheological properties, cohesiveness, and plasticity to yield strong beads. An MCC level at 30% was selected and it was found to provide beads with acceptable sphericity and support a robust manufacturing process. Because LDEE-S is more stable in acidic environment, in order to reduce the LDEE degradation inside the beads during the long release duration, a 5% fumaric acid is added in the formulation to lower the microenvironment pH. An extra binder povidone at 1% level is also added to the formulation with the intent to provide a more robust extrusion process. The dissolution profile of the core beads is fast, with the complete release within 30 min, as measured in a USP Apparatus 1 with basket speed of 75 rpm in pH 7 phosphate buffer.

To control the release of LDEE-S, the core LDEE-S beads are coated with different release polymers. Eudragit® E100 is swellable and permeable above pH 5. It is used as an inner coating to slowly release drug at intestinal pH. As such, the use of Eudragit® E100 coating results in a controlled release of LDEE-S. Furthermore, to protect the Eudragit® E layer as well as to direct the release of LDEE-S to the more alkaline region (i.e., intestinal region and not the stomach region), an enteric coating is applied as an outer coat.

Development of Eudragit® E100 Coated LDEE-S Beads

Prototype formulations with different Eudragit® E100 coating content were developed and evaluated based on the in vitro dissolution profiles in pH 7 phosphate buffer solution. Analysis of the effect of coating thickness on LDEE release indicates that increasing the coating level decreases the in vitro release of active pharmaceutical ingredient (API) and although polymer has the sustained-release effect, its permeability is relatively large, thus a thick coating is required to prepare formulations with longer release duration (T90>5 hr).

In the final polymer coating formulation, talc was also added as a lubricant to facilitate the fluid bed coating process at a ratio of Eudragit® E100/talc at 10/1.

Development of Enteric Coating of Eudragit® E100 Coated LDEE-S Beads

Initially, the enteric coating chosen at the development stage was Eudragit® SI00 and LI00 at a ratio of 2:1, and the ratio among polymer and other components was Eudragit® polymer:triethyl citrate (TEC):Talc ratio of 7:2:1.

The in vitro dissolution profiles of prototype enteric coated beads (already coated with Eudragit® E100 at a coating level of 65% w/w) coated with different levels of enteric film. The results showed that a coating level of 23% provides an adequate acid protection with less than 5%

LDEE released in acidic medium. Further, with less enteric coating level (<10%), there is ~20% LDEE released in acidic medium, and no significant difference in drug release profiles when coated at 5% or 10%.

When the dissolution was done in pH 1 solution for 2 hr and then switch to pH 7 buffer, even with outer enteric coating layer, the permeability of inner Eudragit® E100 layer may increase after 2 hr in pH 1.0 medium, since T90 was around 6.5 hr in pH 7 buffer for Eudragit® E coated beads but shortened to ~4.5 hr in pH 7 buffer for enteric coated beads after switch over of dissolution medium.

For IPX203-B12-01, enteric polymer coatings that can dissolve at lower pH were also developed, in which Eudragit® L100-55 (dissolve above pH 5.5) was used instead of Eudragit® S100 and L100. The ratio among polymer and other components in the coating formulation was Eudragit® L100-55:TEC:Talc of 6:1:3.

Dissolution Medium pH Effect on LDEE Release from Enteric Coated Beads

The effect of pH on the release of LDEE from the LDEE-S core beads coated with Eudragit® E (65% w/w) and enteric coat (Eudragit® S100/L100 at 2/1) was conducted at pH 1.0 solution for 2 hr and then switch to pH 6.6, 6.8, 7.0 buffer solutions.

The results indicated that with less enteric layer coated (10%) or thinner enteric outer coating, drug release was earlier, and conversely, with a thicker enteric outer coating (23%), drug release was delayed at all pH's compared to the thinner enteric outer coated LDEE-S core beads. Further, with less or thinner enteric outer coating, there was no effect on drug release when pH changed from 6.6 to 6.8, and the drug release was slower when pH changed to 7.0. However, when thicker enteric coat layer was applied (23%), there was no effect on drug release when pH changed from 6.8 to 7.0, but the drug release was much slower when pH changed to 6.6. Additionally, the pH value in dissolution medium can affect drug release profiles through its effect on both enteric coating layer dissolution and Eudragit® E layer permeability. When enteric coat layer is thin, its dissolution is fast and the pH effect on Eudragit® E is more a rate-limiting factor. Since Eudragit® E permeability decreases with increasing pH, slower release was observed in pH 7.0 medium. However, with a thicker enteric coat, the dissolution of the enteric layer is much slower and become a rate-limiting step. With a combination of Eudragit® S100 and L100 at a ratio of 2/1, its dissolution at lower pH (pH 6.6) is much slower than at pH above 6.8. Thus the drug release is much slower in pH 6.6 medium with a thicker enteric coating.

Final Formulation of LDEE-S Beads for IPX203-B12-01

The test formulations for IPX203-B12-01 are summarized in Table 1. The composition of the formulations of LDEE-S beads (IPX203-C0004, IPX203-C0005 and IPX203-C0006) is summarized in Table 2. FIG. 2 shows the in vitro dissolution profiles of those formulations. IPX203-C0066 was coated with 10% (w/w) enteric coat (Eudragit® S100/L100 at 2/1), which released ~20% drug in the first 2 hr in pH 1.0 solution. After dissolution medium switch to pH 7 buffer, drug was controlled released over a period T90~3 hr. A better acidic protection for IPX203-0004 and IPX203-C0005 was observed due to their thicker enteric coat layer (25% w/w, Eudragit® L100-55). Formulations IPX203-C0004 has a thinner Eudragit® E100 layer of coating compared to IPX203-C0005, and has T90~3 hr in pH 7 buffer. IPX203-C0005 provided longer release duration (T90~5 hr in pH 7 buffer).

TABLE 1

Test Formulations of IPX203 Prototype Capsule in Single Dose Relative Bioavailability (BA) Studies IPX203-B12-01*.

| Test Formulation | Study | LDEE (mg/2 capsules) |
|---|---|---|
| IPX203-C0004 | IPX203-B12-01 | 228 |
| IPX203-C0005 | | 228 |
| IPX203-C0006 | | 228 |

*Carbidopa was dosed as commercial product Lodosyn ® 25 mg/tablet with the dosing regimen: 25 mg at T = 0 and 6.25 mg (¼ tablet) at T = 4 hr.

TABLE 2

Composition of Final Formulation of LDEE-S Beads for IPX203-B12-01

| | Composition (w/w %) | | |
|---|---|---|---|
| Ingredient | IPX203-C0004 | IPX203-C0005 | IPX203-C0006 |
| Levodopa Ethyl Ester Succinate, Dihydrate | 31.76 | 28.50 | 32.39 |
| Microcrystalline Cellulose, NF | 14.66 | 13.15 | 14.95 |
| Fumaric Acid, NF | 2.44 | 2.19 | 2.49 |
| Povidone, USP (Plasdone, K-29/32) | 0.49 | 0.44 | 0.50 |
| Amino Methacrylate Copolymer, NF (Eudragit ® E 100) | 27.14 | 31.74 | 36.08 |
| Methacrylic Acid Copolymer, Type C, NF (Eudragit ® L 100-55) | 11.88 | 11.88 | — |
| Methacrylic Acid Copolymer, Type A, NF (Eudragit ® L 100) | — | — | 2.10 |
| Methacrylic Acid Copolymer, Type B, NF (Eudragit ® S 100) | — | — | 4.20 |
| Triethyl Citrate, NF | 1.98 | 1.98 | 1.80 |
| Talc, USP | 9.64 | 10.12 | 5.50 |
| Total | 100.0 | 100.0 | 100.0 |

II. In Vivo Results of IPX203-B12-01

The in vivo performance of the prepared formulations IPX203-C0004, IPX203-C0005 and IPX203-C0006 has been evaluated in healthy volunteers in a relative bioavailability analysis of IPX203-B12-01. The study design was a randomized, single-dose, crossover study in normal, healthy volunteers under fasting condition.

FIG. 3 shows the plasma profile for the multi-particulate formulations IPX203-C0004, IPX203-C0005 and IPX203-C0006 in comparison with Sinemet® CR. All the IPX 203 multi-10 particulate formulations comprise Eudragit® E coating. The relative bioavailability parameters are provided in Table 3. Comparison of the LD plasma concentration profile of the tested formulations to the reference product Sinemet® CR indicate that both IPX203-C0005 and IPX203-C0006 showed sufficient AUC but more extended effect than Sinemet® CR, Further, the difference of Tmax between IPX203-C0004 and IPX203-C0005 corresponds well with their difference in in vitro dissolution profiles. Also, although the in vitro release profiles for IPX203-C0004 and IPX203-C0006 showed similar T90 (~3 hr) after switch to pH 7 buffer, IPX203-C0006 showed more delayed effect in vivo. Additionally, the results show that IPX203-C0006 has Cmax and AUC comparable to those of Sinemet® CR.

TABLE 3

Relative LD Bioavailability Parameters of IPX203 Capsules Tested in Bioavailability Analysis of IPX203-B12-01 (n = 15).

| Test Formulation | CD-LDEE (mg)[a] | | % Ratio of Test/ Sinemet ® CR | | Duration LD Concentration >50% Cmax (h)[b] |
|---|---|---|---|---|---|
| | LDEE | CD | AUC0-∞ | Cmax | |
| IPX203-C0004 | 228 | 31.25 | 80 | 86 | 2.9 (3.3) |
| IPX203-C0005 | 228 | | 97 | 97' | 3.15 (3.25) |
| IPX203-C0006 | 228 | | 87 | 104 | 3.25 (3.25) |

[a]LDEE 228 mg is equivalent to LD 200 mg.
[b]Sinemet ® CR tablet $t_{max}$ = 2.5 hr Example 2

I. Processing Procedures for Levodopa Ethyl Ester Succinate (LDEE-S)/Carbidopa (CD) Capsules for IPX203 B13-01

Preparation of Core Beads for IPX203-C0012, IPX203-C0013 and IPX203-C0016

Required amounts of LDEE-S-Dihydrate, Microcrystalline Cellulose, Fumaric acid, Povidone K29-32, ethanol and Purified Water were dispensed. The alcohol and the purified water were charged into a container and stirred using stir bar, Povidone was slowly added into the ethanol/water mixed solvent. Mixing continued until the Povidone was completely dissolved, and the spray pump was calibrated to the target granulation spray rate.

LDEE-S-Dihydrate, Microcrystalline Cellulose, Fumaric acid, and Povidone were charged into a high shear granulator and dry mixed for 1-5 minutes at impeller speed of 75 rpm and chopper speed of 1000 rpm. The Povidone solution was sprayed into the granulation bowl and granulation continued with either ethanol or water as necessary. The granules were wet mixed for 2 minutes, after the spraying was completed.

The wet granules were extruded using the extruder (MG 55 Multi Granulator) equipped with a 0.8 mm hole size screen at extruder speed of 55 rpm. The extrudates were collected into double polyethylene-lined bags. The collected extrudate was weighed and adjusted in the quantities ranging from 180-240 g per load.

One load of the weighed extrudate was charge into a spheronizer equipped with a 3 mm cross hatch disc. The extrudate was spheronized at a spheronisation speed of 1400 rpm for 1-10 mins. The spheronized beads were discharge into double PE bags. The remaining extrudate were spheronized until all the double polyethylene-lined bags are completed.

The wet beads were dried in a fluid bed drier (Glatt GPCP-1) at an Inlet temperature of 35±10° C. until Loss on Drying is not more than 5.0%. The steps above were repeated until additional sub loads have been processed.

The dried beads were passed through a mechanical sieve (Vibroscreen) equipped with a 24-MG mesh screen at the bottom, 18-MG mesh screen in the middle, and 16-MG mesh screen at the top. The beads that remained on 18-US mesh and 24-MG mesh screens were collected into double polyethylene-lined bags.

Rate-Controlling Membrane Coating for IPX203-C0012 and IPX203-C0013

IPX203-C0012 Beads

Batch yield was determined. Based on the batch yield, the required amounts of Cellulose Acetate (CA) and Polyethylene Glycol 3350 (PEG3350) at weight ratio (CA/PEG) of 95/5 and Acetone/Purified Water (95/5 w/w) were calculated and dispensed. The Acetone was dispensed into a stainless steel container and stirred using stir bar. While stirring, Cellulose Acetate (CA) was added slowly into the vortex of the solvent and mixing was continued until the copolymer completely dissolved.

The Purified Water was dispensed into another stainless steel container and was stirred using a stir bar. While stirring, Polyethylene Glycol 3350 (PEG3350) was added slowly into the vortex of the purified water solvent and mixing was continued until the copolymer completely dissolved. While stirring, PEG solution was added quickly into the CA solution and mixing was continued until the solution was clear. Spray pump was calibrated to the target coating spray rate of the peristaltic pump using the clear solution and the core beads were coated using Glatt GPCG 1 equipped with a Wurster insert at Inlet air temperature of 33±10° C., Atomization air pressure of 1.0-2.0 bars and Wurster partition height of ^0-40 mm. During coating, the inlet air temperature, exhaust flap, and spray rate were adjusted to maintain the exhaust air temperature between 30±5° C.

After the target amount of coating solution was sprayed, the coated beads were dried at an inlet air temperature of 35±10° C. for 40-60 minutes. The dried beads were passed through a mechanical sieve (Vibroscreen) equipped with a pan at the bottom and a 14-MG mesh screen at the top. and collected the beads that passed through the 14-MG mesh screen were collected in double polyethylene-lined bags. Oversized beads that remained on the 14-MG mesh screen were rejected.

IPX203-C0013 Beads

The procedure for preparing the coating solution and the coating conditions are identical to those for IPX203-C0012 coating. However, the rate-controlling polymer is Cellulose Acetate (CA), and the solvent is Acetone.

Muco-Adhesive Coating for IPX203-C0012, IPX203-C0013 and IPX203-C0016

The batch yield was determined. The required amounts of Amino Methacrylate Copolymer (Eudragit® E100) and Talc were calculated and dispensed at weight ratio of 91/9. Purified Water, Acetone and Isopropyl Alcohol were dispensed at weight ratio of 12/68/20 into a stainless steel container and stirred using stir bar. While stirring, Amino Methacrylate Copolymer (Eudragit® E100) was slowly added into the vortex of the mixed solvent. Mixing continued until the copolymer completely dissolved. While stirring, Talc was slowly dispersed into the vortex of the solution. Mixing continued until the material was completely dispersed. The suspension was continually stirred throughout the coating process.

The spray pump was calibrated to the target coating spray rate of the peristaltic pump using the suspension solution above. The rate-controlling membrane-coated beads for IPX203-C0012 and IPX203-C0013, or the core beads for IPX203-C0016 were coated with the muco-adhesive coating composition Glatt GPCG 1 equipped with a Wurster insert at Inlet air temperature of 35±10° C., Atomization air pressure of 1.0-2.0 bars and Wurster partition height of 15-40 mm. During coating, the inlet air temperature, exhaust flap, and spray rate were adjusted to maintain the exhaust air temperature between 30±10° C.

After the target amount of coating solution was sprayed, the coated beads were dried at an inlet air temperature of 40±10° C. for 60-120 minutes. The dried beads were passed through a mechanical sieve (Vibroscreen) equipped with a pan at the bottom and a 14-MG mesh screen at the top. The beads that passed through 14-MG mesh screen were collected into double polyethylene-lined bags and the oversized beads that remained on the 14-MG mesh screen were rejected.

Enteric Coating for IPX203-C0012, IPX203-C0013 and IPX203-C0016

The batch yield was determined. Based on the batch yield, the required amounts of Triethyl Citrate, Talc and an enteric copolymer, either Methacrylic Acid Copolymer, Type A, (Eudragit L100)/Methacrylic Acid Copolymer, Type B, (Eudragit® S) at 1/2 weight ratio for IPX203-C0012 and IPX203-C0016 or Eudragit® L100 for IPX203-C00013 were calculated and dispensed. Acetone and Isopropyl Alcohol were dispensed at weight ratio of 40/60 into a stainless steel container and stirred using stir bar. While stirring, the enteric copolymer and Triethyl, Citrate (TEC) were added slowly into the vortex of the mixed solvent and mixing was continued until the enteric copolymer completely dissolved. While stirring, Talc was slowly dispensed into the vortex of the solution and mixing was continued until the material was completely dispersed. The suspension was continuously stirred throughout the coating process. The weight ratio of enteric copolymer/TEC/Talc was 70/20/10.

The spray pump was calibrated to the target coating spray rate of the peristaltic pump using the solution, and the Eudragit® E-coated beads were coated using Glatt GPCG 1 equipped with a Wurster insert at Inlet air temperature of 35±10° C., Atomization air pressure of 1.0-2.0 bars and Wurster partition height of 15-30 mm. During coating, the inlet air temperature, exhaust flap, and spray rate were adjusted to maintain the exhaust air temperature between 30±5° C. After the target amount of coating solution was sprayed, the coated beads were dried at an inlet air temperature of 40±10° C. for 60-120 minutes and the dried beads were passed through a mechanical sieve (Vibroscreen) equipped with a pan at the bottom and a 14-MG mesh screen at the top. The beads that passed through 14-MG mesh screen were collected into double polyethylene-lined bags, and oversized beads that remained on the 14-MG mesh screen were rejected.

Immediate Release Granules (CD/LDEE-S)

The required amount of 27% Carbidopa USP, 49.9% Levodopa Ethyl Ester Succinate-Dihydrate, 12.2% Dibasic Calcium Phosphate Anhydrous, 7.0% Hydroxypropyl Cellulose (Klucel-EXF), and 2.0% Croscarmellose Sodium, (Ac-Di-Sol) were dispensed and charged into the granulation bowl of a high shear granulator. The components were dry-mixed for 1-3 mins at impeller speed between 150-250 rpm and Chopper Speed of 1000 rpm. Purified Water was sprayed at a desired flow rate into the granulation bowl until consistent wet mass was reached. The water/dry blend weight ratio was between 0.20-0.40. The granules were wet-mixed for additional 1-5 minutes, after the spraying was completed. The wet granules were charged into the top spray product bowl of GPCG1 and dried using GPCG 1 at inlet air temperature of 50° C. until the LOD is less than 6.0%. Inlet air flow was adjusted to maintain the fluidization of the wet granules. The dried granules from the bowl were transferred into clean, double polyethylene-lined containers, and the granules were passed through the Fitzmill equipped with a stainless steel #24 mesh screen at Knife Mode and speed of 2000-3000 rpm. The required amount of Talc was calculated based on the weight of the milled granules and 2% Talc of the immediate release granules. The milled granules and Talc were charged into Pharmatech Miniblender and blended for 5 minutes. The blend was discharged into clean, double polyethylene-lined containers.

Encapsulation

The batch yield was determined. Based on the batch yield, the required amounts of the Enteric Coated Beads and Talc (at weight ratio of 99/1) were calculated and dispensed. The Enteric Coated Beads and Talc were charged into an appropriated sized plastic bag and manually blended by shaking the plastic bag for 10 minutes. The blend and Immediate Release Granules (CD/LDEE-S) were encapsulated with 00 size gelatin capsules, using MG Flexalab Encapsulator. For IPX203-C0016, the blend was encapsulated but the Immediate Release Granules (CD/LDEE-S) were not. Table 4 shows the target fill weight for IPX203-C0012, IPX203-C0013 and IPX203-C0016 and Table 5 lists the composition of IPX203-C0012, IPX203-C0013 and IPX203-C0016.

TABLE 4

Target Fill Weight of IPX203-C0012, IPX203-C0013 and IPX203-C0016

| | Target Fill Weight (mg/Capsule) | |
|---|---|---|
| | Enteric-coated Beads | Immediate release Granules |
| IPX203-C0012 | 389.5 | 200.0 |
| IPX203-C0013 | 412.0 | 200.0 |
| IPX203-C0016 | 252.6 | N/A |

TABLE 5

Formulation Composition of IPX203-C0012, IPX203-C0013 and IPX203-C0016

| | IPX203-00012 | | 1PX203-00013 | | IPX203-00016 | |
|---|---|---|---|---|---|---|
| Ingredient | Amount (mg/capsule) | % (w/w) | Amount (mg/capsule) | % (w/w) | Amount (mg/capsule) | % (w/w) |
| Carbidopa, USP | 54.0 | 9.2 | 54.0 | 8.8 | | |
| Levodopa Ethyl Ester Succinate, Dihydrate | 306.4 | 52.0 | 306.4 | 50.1 | 81.8 | 32.4 |
| Microcrystalline Cellulose, NF | 95.4 | 16.2 | 95.4 | 15.6 | 37.7 | 14.9 |
| Amino Methacrylate Copolymer, NF (Eudragit® E100) | 33.1 | 5.6 | 33.4 | 5.5 | 91.1 | 36.1 |
| Fumaric Acid, NF (Fine Granules) | 15.9 | 2.7 | 15.9 | 2.6 | 6.3 | 2.5 |
| Cellulose Acetate, NF (CA-398-10 NF) | 9.1 | 1.5 | 12.9 | 2.1 | 0.0 | |
| Talc, USP | 13.1 | 2.2 | 15.2 | 2.5 | 13.9 | 5.5 |
| Methacrylic Acid Copolymer, Type B, NF (Eudragit® S100) | 8.5 | 1.4 | | | 10.6 | 4.2 |

TABLE 5-continued

Formulation Composition of IPX203-C0012, IPX203-C0013 and IPX203-C0016

| Ingredient | IPX203-00012 Amount (mg/capsule) | % (w/w) | IPX203-00013 Amount (mg/capsule) | % (w/w) | IPX203-00016 Amount (mg/capsule) | % (w/w) |
|---|---|---|---|---|---|---|
| Methacrylic Acid Copolymer, Type A, NF (Eudragit® L100) | 4.3 | 0.7 | 25.9 | 4.2 | 5.3 | 2.1 |
| Triethyl Citrate, NF | 3.7 | 0.6 | 7.4 | 1.2 | 4.5 | 1.8 |
| Povidone, USP (Plasdone, K-29/32) | 3.2 | 0.5 | 3.2 | 0.5 | 1.3 | 0.5 |
| Polyethylene Glycol, NF | 0.5 | 0.1 | | | | |
| Dibasic Calcium Phosphate, Anhydrous | 24.3 | 4.1 | 24.3 | 4.0 | | |
| Hydroxypropyl Cellulose, NF (Klucel-EXF) | 14.0 | 2.4 | 14.0 | 2.3 | | |
| Croscarmellose Sodium, NF (Ac-Di-Sol) | 4.0 | 0.7 | 4.0 | 0.7 | | |
| Total | 589.5 | 100.0 | 612.0 | 100.0 | 252.6 | 100.0 |

*54 mg of Carbidopa, USP is equivalent to 50 mg of Carbidopa anhydrate.
**306 mg of Levodopa Ethyl Ester Succinate-Dihydrale is equivalent to 228 mg of Levodopa Ethyl Ester and to 200 mg Levodopa.

II. Processing Procedures for Manufacturing Entacapone Capsules for IPX203 B13-01

Preparation of Core Beads for IPX203-C0014 Capsule

The required amount of Entacapone, Microcrystalline Cellulose, Povidone K29-32 and Purified Water were dispensed. The purified water was charged into a container and stirred using a stir bar, the Povidone (1.0% of the solid blend) slowly added into the water at Povidone/Water weight ratio of 6/133.2 and mixing continued until the Povidone was completely dissolved. The spray pump was calibrated to the target granulation spray rate (23 g/min), and 84.0% Entacapone and 15.0% Microcrystalline Cellulose were charged into a high shear granulator and were dry mixed for 1-5 minutes at impeller speed of 200-300 rpm and chopper speed of 1400-1600 rpm. The solution was sprayed into the granulation bowl until all the solution was sprayed, and granulation was continued with Purified Water as necessary. The granules were wet-mixed for 2 minutes, after the spraying was completed. Then the wet granules were extruded using the extruder (MG 55 Multi Granulator) equipped with a 0.8 mm hole size screen at extruder speed of 50 rpm. The extrudates were collected into double polyethylene-lined bags. Further, the collected extrudate were weighed and adjusted in the quantities ranging from 200-210 g per load.

One load of the weighed extrudate was charged into a spheronizer equipped with a 3 mm cross hatch disc and spheronized at spheronisation speed of 1000 rpm for 1-2 mins. The spheronized beads were discharged into double PE bags. The wet beads were dried in a fluid bed drier (Glatt GPCP-1) at an Inlet temperature of 35±10° C. until Loss on Drying was not more than 5.0%. The dried beads were passed through a mechanical sieve (Vibroscreen) equipped with a pan at the bottom, 24-MG mesh screen in the middle, and 16-MG mesh screen at the top. The beads that were retained on 24-MG mesh were collected into double polyethylene-lined bags, and the beads on the pan and 16-MG mesh screen were rejected.

Enteric Coating for IPX203-C0014

The required amounts of Triethyl Citrate, Talc, Methacrylic Acid Copolymer Dispersion, NF (Eudragit® L30D-55) and Water were calculated and dispensed. The Purified Water was dispensed into a stainless steel container and stirred using a stir bar. While stirring, Triethyl Citrate (TEC[1]), Talc and the enteric copolymer dispersion were slowly added into the vortex of Purified Water, and mixing was continued until the material was completely dispersed. The suspension was stirred throughout the coating process. The weight ratio of enteric copolymer/Talc/TEC was 63.0/30.7/6.3.

The spray pump was calibrated to the target coating spray rate of the peristaltic pump using the solution, and the core beads were coated using Glatt GPCG 1 equipped with a Wurster insert at Inlet air temperature of 35±10° C., Atomization air pressure of 1.0-2.0 bars and Wurster partition height of 15-30 mm. During coating, the inlet air temperature, exhaust flap, and spray rate were adjusted to maintain the exhaust air temperature between 30±5° C.

After the target amount of coating solution was sprayed, the coated beads were dried at an inlet air temperature of 30±10° C. until the moisture level was below 5%. The dried beads were passed through a mechanical sieve (Vibroscreen) equipped with a pan at the bottom and a 12-MG mesh screen at the top. The beads that passed through the 12-MG mesh screen were collected into double polyethylene-lined bags, and the oversized beads that remained on the 12-MG mesh screen were rejected.

Encapsulation for IPX203-C0014

The required amounts of the Enteric Coated Beads and Talc (at weight ratio of 99/1) were calculated and dispensed, and the Enteric Coated Beads and Talc were charged into an appropriate sized plastic bag. The beads and Talc were manually blended by shaking the plastic bag for at least 5 minutes. The blend was encapsulated with 00 size gelatin capsules, using MG Flexalab Encapsulator. The target fill weight was 505 mg. Table 6 lists the composition of IPX203-C0014.

TABLE 6

Formulation Composition of Entacapone Capsule (IPX203-C0014)

| Ingredient | % (w/w) | Amount (mg/capsule) |
|---|---|---|
| Entacapone | 79.2 | 400.0 |
| Microcrystalline Cellulose, NF (Avicel PH-101) | 14.1 | 71.4 |

TABLE 6-continued

Formulation Composition of Entacapone Capsule (IPX203-C0014)

| Ingredient | % (w/w) | Amount (mg/capsule) |
|---|---|---|
| Povidone, USP (Plasdone, K-29/32) | 1.0 | 4.8 |
| Methacrylic Acid Copolymer Dispersion, NF (Eudragit ® L30D-55) | 3.0 | 15.0 |
| Talc, USP | 2.4 | 12.3 |
| Triethyl Citrate, NF | 0.3 | 1.5 |
| Total | 100.0 | 505.0 |

III. In Vitro Release Profiles of Final LE (EE-S-Dihydrate Dosage Forms for Pharmacokinetic (IPX203-B13-01)

Table 7 lists the test regimen for the 5-arm cross-over PK analysis (IPX203 B13-01).

TABLE 7

Dosing Regimen for IPX203 B13-01

| Regimen | Dosage Form | CD/ capsule | LD/ capsule | Entacapone/ capsule |
|---|---|---|---|---|
| Regimen A | IPX203-C0012 | 50 mg | 200 mg* | N/A |
| Regimen B | IPX203-C0012 + IPX203-C0014 | 50 mg | 200 mg* | 400 mg |
| Regimen C | IPX203-C0013 + IPX203-C0014 | 50 mg | 200 mg* | 400 mg |
| Regimen D | IPX203-C0013 + IPX203-C0016 + IPX203-C0014 | 50 mg | 255.6 mg* | 400 mg |
| Regimen E | Stalevo ® 150 mg | 37.5 mg | 150 mg | 200 mg |

*LD equivalent dose based on total amount of LDEE-S-Dihydrate in the formulation The in vitro release profiles of the regimen A-D were measured using USP I dissolution method at agitation speed of 75 rpm in Simulated Gastric Fluid (pH 1.0) for first 2 hrs and followed by in Simulated Intestinal Fluid (pH 7.0). FIG. 4 shows the release profiles of these test regimens.

The T90 (time duration for 90% of LDEE-S-Dihydrate released) is approximately 3 hr, 4.5 h and 6 hrs for Regimen B, C and D, respectively. The LDEE-S-Dihydrate capsule (C0012) was used in both Regimen A and Regimen B.

VI. In Vivo Evaluation (IPX203-B13-01)

The in vivo performance of the prepared dosage forms IPX203-C00012, IPX203-C00013 and IPX203-C00014 and IPX203-C0016 has been evaluated in 12 healthy volunteers under fasted condition in a relative bioavailability analysis of IPX203-B13-01. The four test treatments were:

Regimen A: C0012
Regimen B: C0012+C0014
Regimen C: C0013+C0014
Regimen D: C0013+C0016+C0014
Regimen E: Stalevo 150 (Reference)
Where
C0012 contained 228 mg LDEE ER beads with T90-3 hrs and 50 mg CD
C0013 contained 228 mg LDEE ER beads with T90-5 hrs and 50 mg CD
C0014 contained 400 mg enteric-coated entacapone
C0016 contained 77 mg LDEE ER beads with T90-12 hrs FIG. 5 shows the levodopa plasma profiles for all these regimens. Based on the in vivo plasma profiles depicted in FIG. 5, the in vivo plasma profiles correlates well with the in vitro dissolution profiles depicted in FIG. 4. FIG. 5 demonstrates that Regimen D has the longest therapeutic coverage and a constant plasma profile.

Example 3

Prepared Carbidopa Beads

The core beads of CD beads were formulated based on the granulation-extrusion-spheronisation technology. 30 w/w % MCC was used in the core seed formulation. No controlled release coating layer was needed. CD core beads was enteric-coated with the enteric coating formulation comprising EUDRAGIT® SI00 and LI00 at a ratio of 2:1. The enteric coating level was 5%.

Table 8 summarized the composition of final formulation of CD beads.

TABLE 8

Composition of Formulation of CD Beads

| Ingredient | Composition (w/w %) |
|---|---|
| Carbidopa | 66.44 |
| Microcrystalline Cellulose, NF | 28.47 |
| Methacrylic Acid Copolymer, Type A, NF (Eudragit ® L 100) | 1.14 |
| Methacrylic Acid Copolymer, Type B, NF (Eudragit ® S 100)' | 2.35 |
| Triethyl Citrate, NF | 1.00 |
| Talc, USP | 0.60 |
| Total | 100.0 |

Example 4

The preparation procedure in Example 1 was repeated in this example, except the coating compositions. The core beads were coated first with either cellulose acetate polymer or a combination of Hypromellose and ethylcellulose. The coated beads were further coated with chitosan or polycarbophil or Eudragit® E100. After the second layer coating, the beads were further coated with Eudragit® L100-55. Table 9 shows the composition of four formulations IPX203-C0007, IPX203-C0008, IPX203-C0009 and IPX203-C0010.

TABLE 9

Composition of Formulations of LDEE-S Beads Using Chitosan or Polycarbophil as Muco-adhesive Polymers

| | Composition (w/w %) | | | |
|---|---|---|---|---|
| Ingredient | IPX203-C0007 | IPX203-C0008 | IPX203-C0009 | IPX203-C0010 |
| Levodopa Ethyl Ester Succinate, Dihydrate | 39.45 | 45.18 | 31.14 | 45.30 |
| Microcrystalline Cellulose, NF | 18.21 | 20.85 | 14.37 | 20.91 |
| Fumaric Acid, NF | 3.03 | 3.48 | 2.40 | 3.48 |
| Povidone, USP (Plasdone, K-29/32) | 0.61 | 0.70 | 0.48 | 0.70 |
| Hypromellose, Type 2910, USP (Pharmacoat 606, 6 cps) | 2.82 | — | 2.23 | 4.22 |
| Ethylcellulose, NF (Ethocel, Standard-10 FP Premium) | 11.28 | — | 8.90 | 16.89 |
| Polycarbophil, USP (Noveon ® AA-1) | 3.77 | — | — | 4.57 |
| Cellulose Acetate, NF (CA-398-10 NF) | — | 4.21 | — | — |

TABLE 9-continued

Composition of Formulations of LDEE-S Beads Using Chitosan or Polycarbophil as Muco-adhesive Polymers

| Ingredient | Composition (w/w %) | | | |
|---|---|---|---|---|
| | IPX203-C0007 | IPX203-C0008 | IPX203-C0009 | IPX203-C0010 |
| Chitosan, NF (ChitoPharm ® S) (Material #50222178) | — | 3.74 | — | — |
| Glacial Acetic Acid, USP | — | 1.01 | — | — |
| Amino Methacrylate Copolymer, NF (Eudragit ® E 100) | — | — | 17.86 | — |
| Methacrylic Acid Copolymer, Type C, NF (Eudragit ® L100-55) | 11.91 | 11.91 | 11.90 | 1.76 |
| Triethyl Citrate, NF (PG) | 1.99 | 1.99 | 1.98 | 0.29 |
| Talc, USP | 6.94 | 6.93 | 8.73 | 1.87 |
| Total | 100.0 | 100.0 | 100.0 | 100.0 |

Example 5

I. Formulations for IPX203-B14-01 Biostudy

Four test formulations were evaluated in biostudy IPX203-B14-01. For IPX203-C0023, -C0024, and -C0025 formulations, there were two components in one capsule. For IPX203-C0026, there were three components in one capsule. Table 10 below showed the formulation information for each product, and Tables 11-13 showed formulation composition for each component.

TABLE 10

Test Formulations for Relative Bioavailability Study IPX203-B14-01

| Test Formulation | Component I: IR | | Component II: LD ER | Entacapone (ENT) Component |
|---|---|---|---|---|
| | CD (mg) | LD (mg) | Prototype/LD (mg) | ENT (mg) |
| IPX203-C0023 | 50 | 80 | Prototype I/280 | 0 |
| 1PX203-C0024 | | | Prototype III/280 | |
| IPX203-C0025 | | | Prototype II/280 | |
| IPX203-C0026 | | | Prototype II/280 | 200 |
| Stalevo ® 100 (Reference) | | | CD/LD/ENT (25/100/200 mg) | |

TABLE 11

Composition of Prototype Formulations of IPX203 Component II

| Ingredient | Composition (%) | | |
|---|---|---|---|
| | Prototype I | Prototype II | Prototype III |
| Core bead | | | |
| levodopa | 65.26 | 62.15 | 61.03 |
| Microcrystalline Cellulose | 8.82 | 8.40 | 8.25 |
| Mannitol, | 8.82 | 8.40 | 8.25 |
| Sodium Lauryl Sulfate | 4.41 | 4.20 | 4.12 |
| Povidone | 0.88 | 0.84 | 0.82 |

TABLE 11-continued

Composition of Prototype Formulations of IPX203 Component II

| Ingredient | Composition (%) | | |
|---|---|---|---|
| | Prototype I | Prototype II | Prototype III |
| CA/Copovidone layer (1st layer) | | | |
| Cellulose Acetate | — | 1.89 | 1.85 |
| Copovidone | — | 2.31 | 2.27 |
| Eudragit ® E100 layer (2n<l layer) | | | |
| Eudragit ® E100 | 6.42 | 6.41 | 3.93 |
| Talc | 0.63 | 0.65 | 0.40 |
| Enteric layer (3rd layer) | | | |
| Eudragit ® L100 | 3.34 | 3.33 | 6.36 |
| Triethyl Citrate | 0.96 | 0.95 | 1.81 |
| Talc | 0.47 | 0.48 | 0.91 |
| Total | 100.0 | 100.0 | 100.0 |

TABLE 12

Composition for Component I Formulation

| Ingredient | Composition (w/w %) |
|---|---|
| Carbidopa | 35.86 |
| Levodopa | 53.14 |
| Croscarmellose Sodium | 7.00 |
| Povidone | 3.00 |
| Magnesium Stearate | 1.00 |
| Total | 100.0 |

TABLE 13

Formulation Composition for Entacapone Component

| Ingredient | % (w/w) |
|---|---|
| Entacapone | 73.15 |
| Microcrystalline Cellulose, NF (Avicel PH-101) | 14.25 |
| Povidone, USP (Plasdone, K-29/32) | 1.90 |
| Sodium Starch Glycolate | 3.80 |
| Sodium Lauryl Sulfate, NF | 1.90 |
| Methacrylic Acid Copolymer, Type A, NF (Eudragit ® LI00) | 3.50 |
| Talc, USP | 0.50 |
| Triethyl Citrate, NF | 1.00 |
| Total | 100.0 |

II. Processing Procedures for Manufacturing IPX203 Capsules for IPX203 B14-01 Biostudy Preparation of Component I Povidone was dissolved in the purified water completely, and then the spray pump with povidone solution was calibrated to the target granulation spray rate (40 mL/min). CD, LD, Croscarmellose Sodium were charged into a high shear granulator and dry mixed for 1-5 minutes at impeller speed of 150 rpm and chopper speed of 1800 rpm. While continue mixing, the solution from Step 1 was sprayed into the granulation bowl until all the solution is sprayed, and granulation was continued with purified water if necessary. The granules were collected, and the wet granules were dried in a fluid bed drier (Glatt GPCP-1) at an Inlet temperature of 65° C. until Loss on Drying is not more than 2.5%. The dried granules were passed through Fitzmill, and the material that passes through 30 mesh screen was collected. The collected material was blended with magnesium stearate.

Alternative Preparation of Carbidopa-Containing Granules or Beads

In order to avoid potential carbidopa degradation during wet granulation process, a dry granulation process by roller compaction was developed. In this formulation, shown in Table 14, the procedures are described as below.

Appropriate amount of carbidopa, levodopa, microcrystalline cellulose, and croscarmellose sodium were charged into a suitable mixer. The materials were dry mixed for an appropriate time and then charged into roller compactor at the controlled speed to start the roller compaction process. After roller compaction, the collected compacted sheets of materials were blended with colloidal silicon dioxide for appropriate time, and then milled into dried granules using a suitable mill. Finally the milled granules were blended with magnesium stearate in the blender.

TABLE 14

Composition for Levodopa/Carbidopa IR Granules by Dry Granulation Method

| Ingredient | Composition (w/w %) |
|---|---|
| Carbidopa | 37.0 |
| Levodopa | 35.0 |
| Microcrystalline Cellulose | 20.0 |
| Croscarmellose Sodium | 4.0 |
| Colloidal Silicon Dioxide | i 3.0 |
| Magnesium Stearate | 1.0 |
| Total | 100.0 |

The amount and ratio of carbidopa and levodopa may be adjusted as desired, so long as performance of the dried granules or beads are not compromised.

Similarly, controlled release beads containing carbidopa may be prepared by a dry granulation method as provided through the incorporation of rate-controlling excipient, muco-adhesive polymer, and/or enteric coat. Entacapone-containing beads or granules may also be prepared by a dry granulation method.

Preparation of Component II
Preparation of Core Beads for Component II

Povidone was dissolved in the purified water completely, and then calibrate the spray pump with povidone solution to the target granulation spray rate (18 mL/min). LD, Microcrystalline Cellulose, Mannitol and Sodium Lauryl Sulfate were charged into a high shear granulator and dry mixed for 1-5 minutes at impeller speed of 250 rpm and chopper speed of 1800 rpm. The solution from Step 1 was sprayed into the granulation bowl until all the solution is sprayed, and granulation with purified water was continued as necessary. The wet granules were extruded using the extruder (MG 55 Multi Granulator) equipped with a 0.9 mm hole size screen at extruder speed of 75 rpm. The extrudates were collected, and the extrudates so collected were charged into a spheronizer equipped with a 3 mm cross hatch disc. The extrudates were spheronized at speed of 800 rpm for 1-2 mins. The wet beads were dried in a fluid bed drier (Glatt GPCP-1) at an Inlet temperature of 65±10° C. until Loss on Drying is not more than 2.5%. The dried beads were passed through a mechanical sieve (Vibroscreen) equipped with a 24-MG mesh screen at the bottom, and 16-MG mesh screen at the top. The beads that remained on the 24-MG mesh screens were collected into double polyethylene-lined bags, and the oversized and undersized beads were discarded.

CA/Copovidonc Layer Coating (for Prototype 11 and III for Component II)

Cellulose acetate and copovidone (Kollidon VA64) were dissolved into the mixture of acetone and isopropyl alcohol (IPA) solution (acetone/lPA at weight ratio of 4/1) completely. The pump was calibrated and set at the target spray rate of 15 g/min for the coating. The core beads from above were coated using Glatt GPCG 2 equipped with a Wurster insert at Inlet air temperature of 35° C., Atomization air pressure of 2.0 bars and Wurster partition height of 30 mm. During coating, the inlet air temperature and spray rate were adjusted to maintain the exhaust air temperature between 25±5° C. After the target amount of coating solution was sprayed, the coated beads were dried at an inlet air temperature of 35° C. for 30 minutes. The dried beads were passed through a mechanical sieve (Vibroscreen) equipped with a pan at the bottom and a 14-MG mesh screen at the top. The beads that passed through 14-MG mesh screen were collected and the oversized beads were rejected.

Eudragit® E100 Layer Coating

Acetone, IPA and purified water (at weight ratio acetone/IPA/water of 68/20/12) were dispensed into a stainless steel container and begin stirring using stir bar. While stirring, Triethyl citrate, Amino Methacrylate Copolymer (Eudragit® E100) were slowly added into the vortex of the mixed solvent. The mixing was continued until the copolymer completely dissolved. While stirring, Talc was slowly dispersed into the vortex of the solution. Mixing was continued until the material completely dispersed. The suspension was stirred throughout the coating process. The spray pump was calibrated to the target coating spray rate (10 g/min) using the solution above. The beads (from Prototype I, and Prototype 11 and III) were coated using Glatt GPCG 2 equipped with a Wurster insert at Inlet air temperature of 33° C., Atomization air pressure of 2.0 bars and Wurster partition height of 30 mm. During coating, the inlet air temperature and spray rate were adjusted to maintain the exhaust air temperature between 26±5° C. After the target amount of coating solution was sprayed, the coated beads were dried at an inlet air temperature of 35° C. for 30 minutes. The dried beads were passed through a mechanical sieve (Vibroscreen) equipped with a pan at the bottom and a 14-MG mesh screen at the top. The beads that passed through 14-MG mesh screen were collected, and the oversized beads were rejected.

Enteric (Eudragit® L100) Coating

Acetone and Isopropyl Alcohol were dispensed at weight ratio of 40/60 into a stainless steel container and stirred using a stir bar. While stirring, the enteric copolymer Eudragit® LI00 and Triethyl Citrate (TEC) were slowly added into the vortex of the mixed solvent. Mixing was continued until the enteric copolymer completely dissolved. While stirring, Talc was slowly dispersed into the vortex of the solution. Mixing continued until the material was completely dispersed. The suspension was continually stirred throughout the coating process. The spray pump was calibrated to the target at a coating spray rate (9 g/min) using the solution above. The Eudragit® E-coated beads were coated using Glatt GPCG 2 equipped with a Wurster insert at Inlet air temperature of 35° C., Atomization air pressure of 2.0 bars and Wurster partition height of 30 mm. During coating, the inlet air temperature, and spray rate was adjusted to maintain the exhaust air temperature between 27±5° C. After the target amount of coating solution was sprayed, the coated beads were dried at an inlet air temperature of 38° C.

for 30 minutes. The dried beads were passed through a mechanical sieve (Vibroscreen) equipped with a pan at the bottom and a 14-MG mesh screen at the top. The beads that passed through 14-MG mesh screen were collected, and the oversized beads were rejected.

Preparation of Entacapone Component (for IPX203-C0026)

Povidone was completely dissolved in the purified water. Entacapone, Sodium Starch Glycolate, Sodium Lauryl Sulfate and Microcrystalline Cellulose were charged into a high shear granulator and dry mix for 1-5 minutes at impeller speed of 200-300 rpm and chopper speed of 1400-1600 rpm. The solution was sprayed into the granulation bowl at the spray rate of 19 ml/min until all the solution is used, and granulation continued with Purified Water as necessary. The wet granules were extruded using the extruder (MG 55 Multi Granulator) equipped with a 0.9 mm hole size screen at extruder speed of 55 rpm. The extrudates were collected, and charged into a spheronizer equipped with a 3 mm cross hatch disc. The extrudate were spheronized at a spheronization speed of 650 rpm for 2 mins. The wet beads were dried in a fluid bed drier (Glatt GPCP-1) at an Inlet temperature of 40±5° C. until Loss on Drying is not more than 5.0%. The dried beads were passed through a mechanical sieve (Vibroscreen) equipped with a pan at the bottom, 24-MG mesh screen in the middle, and 16-MG mesh screen at the top. The beads that were retained on 24-MG mesh were collected and the beads on the pan and 16-MG mesh screen were rejected. Acetone and Isopropyl Alcohol were dispensed at weight ratio of 40/60 into a stainless steel container and stirred using a stir bar. While stirring, the enteric copolymer Eudragit® L100 and TEC were slowly added into the vortex of the mixed solvent. Mixing continued until the enteric copolymer completed dissolved. While stirring, Talc was slowly dispersed into the vortex of the solution. Mixing continued until the material was completely dispersed. The suspension was stirred throughout the coating process. The spray pump was calibrated to the target coating spray rate (8 g/min) using the solution. The core beads were coated using Glatt GPCG 1 equipped with a Wurster insert at Inlet air temperature of 35±10° C., Atomization air pressure of 1.5 bars and Wurster partition height of 15-30 mm. During coating, the inlet air temperature, exhaust flap, and spray rate were adjusted to maintain the exhaust air temperature between 27±5° C. After the target amount of coating solution was sprayed, the coated beads were dried at an inlet air temperature of 40° C. for 20 minutes. The dried beads were passed through a mechanical sieve (Vibroscreen) equipped with a pan at the bottom and a 14-MG mesh screen at the top. The beads that passed through the 14-MG mesh screen were collected and the oversized beads were rejected.

Encapsulation

The required amounts of the Component I and Component II Beads and Talc were dispensed. For formulation IPX203-C0026, also Entacapone component beads were also dispensed. Talc was weighed at the weight ratio of beads/Talc at 99/1, and Component II beads and Talc were blended thoroughly. For IPX203-C0026 product, Talc was also weighed at the weight ratio of ENT beads/Talc at 99/1, and Entacapone beads and Talc were blended thoroughly. The Component I granules and Component II beads (from encapsulation section) were encapsulated into size 00 hard gelatin capsules, using MG Flexalab Encapsulator at the target fill weight for IPX203 products IPX203-C0023, -C0024, and -C0025. The Component I granules, Component II beads (from encapsulation section), and entacapone beads (from encapsulation section) were encapsulated into size 00 hard gelatin capsules, using MG Flexalab Encapsulator at the target fill weight for IPX203 products IPX203-C0026.

III. In Vitro LD Release Profiles of Four Formulations for Pharmacokinetic Study (IPX203-B14-01)

The in vitro release profiles of IPX203-C0023, -C0024, -C0025 and -C0026 were measured using USP 1 dissolution method at agitation speed of 75 rpm in Simulated Gastric Fluid (pH 1.0, without enzyme) for first 2 hrs and followed by in Simulated Gastric Fluid (pH 7.0, without enzyme). FIG. 6 shows the release profiles of these four formulations. Formulation IPX203-C0025 and IPX203-C0026 contain the same Component II beads thus having same dissolution profiles. The T90 (time duration for 90% of LD released) is approximately 4 hr, 5 h and 7 hrs for -C0023, -C0025 and -C0026, and -C0024, respectively.

IV. In Vivo Evaluation (Biostudy IPX203-B14-01)

The in vivo performance of the prepared products IPX203-C0023, -C0024, -C0025, and -C0026 has been evaluated in 19 healthy volunteers in a relative bioavailability study IPX203-B14-01. IPX203-B14-01 was a single-center, open-label, randomized, single-dose, five-sequence, five-treatment crossover study. During each treatment period, subjects received a single dose of the assigned study treatment. There was a minimum 5-day washout between treatments. Blood samples were obtained predose and following dosing for approximately 12 hours for measurement of plasma concentrations. Thirty healthy male and female subjects, 18 to 45 years of age at the time of dosing with a body mass index of 18.0 to 30.0 kg/m², inclusive, were enrolled. All treatments were administered with 240 mL of room-temperature water to subjects in a fasted state. Subjects were instructed to swallow the study drugs intact without crushing or chewing. FIG. 7 shows the levodopa plasma profiles for all these regimens, and Table 15 shows the PK parameters relative to Stalevo®.

TABLE 15

PK Parameters for All the Regimens Tested in IPX203 B13-01 Study (n = 19)

| Formulation | % of IPX203 Test Formulation/Stalevo ® | | % of IPX203 Test Formulation/Stalevo ® (normalized by LD dose) | |
|---|---|---|---|---|
| | $AUC_{0-\infty}$ | Cmax | $AUC_{0-\infty}$ | Cmax |
| IPX203-C0023 | 277.3 | 179.4 | 77.0 | 49.8 |
| IPX203-C0024 | 199.1 | 121.4 | 55.3 | 33.7 |
| IPX203-C0025 | 226.9 | 134.0 | 63.0 | 37.2 |
| IPX203-C0026 | 265.9 | 141.6 | 73.9 | 39.3 |

Table 16 shows the duration of time above 50% Cmax for IPX203-C0023, -C0024, -C0025, and -C0026 and conventional formulations.

TABLE 16

Duration of Time Above 50% Cmax
IPX203-C0023, -C0024, -C0025 and -C0026
and Conventional Formulations

| Formulation | N | Median | Mean | % Coefficient of Variation (SD/Mean) |
|---|---|---|---|---|
| IPX203-C0023 | 19 | 4.00 | 4.14 | 29.88 |
| IPX203-C0024 | 19 | 5.38 | 4.84 | 35.94 |
| IPX203-C0025 | 19 | 5.38 | 5.20 | 29.30 |
| IPX203-C0026 | 19 | 4.88 | 5.23 | 36.32 |

$C_{max}$ Values normalized to allow comparison

Comparison of the LD plasma concentration profile of the tested formulations to the reference product Stalevo® indicates that: (1) the IPX203 regimens, based on IPX203-C0023, -C0024, -C0025, and -C0026 formulations, showed more extended effect than Stalevo® (Table 16 and FIG. 7); in addition, the IPX203 formulations showed more extended effect than Sinemet® or Sinemet® CR (Table 16 and FIG. 3; for Sinemet® CR (N=11), T>50% $C_{max}$ is ~3.41 hrs); (2) the IPX203 formulations; namely IPX203-C0023, -C0024, -C0025, and -C0026 formulations, showed relatively flat plasma profiles for LD compared to Stalevo® (FIG. 7); (3) the time duration between 50% of $C_{max}$ to $C_{max}$ for IPX203-C0023, -C0024, -C0025, and -C0026 formulations are much longer than Stalevo®, (approximately 4.1-5.2 hrs for test formulations, compared to 2.3 hrs for Stalevo®); and (4) the variation of the time duration between 50% $C_{max}$ to $C_{max}$ for IPX203-C0023, -C0024, -C0025, and -C0026 formulations is less than Stalevo®.

Example 6

Immediate release granules with the following composition were prepared:

|   | Wt % |
| --- | --- |
| Carbidopa USP* | 46.20 |
| Levodopa USP | 42.80 |
| Croscarmellose Sodium (AC-DI-SOL ®) | 7.00 |
| Povidone, USP (Plasdone K-29/32) | 3.00 |
| Magnesium Stearate | 1.00 |

*monohydrate

The granules were prepared mixing using the procedure similar to that described above in Example 5, preparation of Component 1. Generally, the CD, LD and croscarmellose sodium were mixed in a high shear granulator and wet granulated with a 5 wt % aqueous solution of povidone. After granulation, the wet granules were passed through a Comil with a 0.375 inch screen and dried in a fluidized bed. The dried granules were milled with a Fitzmill equipped with a 30 mesh screen then blended with magnesium stearate.

Example 7

Controlled release particles (beads) with the following composition were prepared:

|   | Wt % |
| --- | --- |
| Core |   |
| Levodopa USP | 61.84 |
| Microcrystalline Cellulose, NF (Avicel PH-101) | 8.36 |
| Mannitol, USP (Mannogern TM 2080 Granular) | 8.36 |
| Sodium Lauryl Sulfate | 4.18 |
| Povidone | 0.84 |
| Controlled Release Coat |   |
| Cellulose acetate, NF (CA-398-10-NF) | 1.88 |
| Copovidone, NF (Kollidon VA64) | 2.30 |
| Muco-Adhesive Coating |   |
| Amino-Methacrylic Acid Copolymer, NF (EUDRAGIT E100) | 6.38 |
| Talc | 0.64 |
| Enteric Coating |   |
| Methacrylic Acid Copolymer, Type A, NF (EUDRAGIT L100) | 3.31 |
| Triethyl Citrate, NF | 0.95 |
| Talc, UPS | 0.47 |
| Blend |   |
| Talc | 0.50 |

The controlled release beads were prepared by a process similar to that described in Example 5, Preparation of Component II. Generally, the LD, microcrystalline cellulose, mannitol, and sodium lauryl sulfate were mixed in a high shear granulator and wet granulated with a 5 wt % aqueous solution of povidone. After granulation, the wet granules were extruded using an extruder equipped with a 0.9 mm hole size screen and the extrudate collected and loaded into a spheronizer equipped with a 3 mm cross hatch disc. The wet spheronized beads were dried in a fluidized bed drier. The dried beads were sieved through 16 MG and 24 MG mesh screens and the beads passing through the 16 MG screen but remaining on the 24 MG screen were collected.

The collected beads were coated with a solution comprising cellulose acetate, copovidone, acetone and isopropyl alcohol using a fluidized bed coating apparatus. After the target coating solution was applied, the controlled release coated beads were dried in the fluidized bed. The dried controlled release beads were sieved through 14 MG and 24 MG mesh screens and the beads remaining on the 24 MG screen were collected. The collected controlled release coated beads were coated with a muco-adhesive solution comprising Eudragit E100, talc, acetone and isopropyl alcohol in the fluidized bed. After the target muco-adhesive coating solution was applied to the controlled release coated beads, the muco-adhesive coated beads were dried in the fluidized bed. The dried muco-adhesive coated beads were coated with an enteric coating solution comprising Eudragit L 100, talc triethyl citrate, acetone and isopropyl alcohol in a fluidized bed. After the target enteric coating solution was applied to the muco-adhesive coated beads, the enteric coated beads were dried in the fluidized bed. The dried enteric coated beads were sieved through 14 MG and 24 MG mesh screens and the beads remaining on the 24 MG screen were collected. The collected beads were blended with talc.

Example 8

The immediate release component of Example 6 and the controlled release beads of Example 7 were blended to create a mixture with 67.49 wt % controlled release beads and 32.51% immediate release granules. The mixture was filled into hard gelatin capsules containing (a) 180 mg LD and 45 mg CD and (b) 270 mg LD and 67.5 mg CD. The CD weight is based on CD anhydrous.

Example 9

Controlled release particles (beads) with the following composition were prepared according to the procedure of Example 7:

| | Wt % |
|---|---|
| Core | |
| Levodopa USP | 60.12 |
| Microcrystalline Cellulose, NF (Avicel PH-101) | 8.12 |
| Mannitol, USP (Mannogern TM 2080 Granular) | 8.12 |
| Sodium Lauryl Sulfate | 4.06 |
| Povidone | 0.80 |
| Controlled Release Coat | |
| Cellulose acetate, NF (CA-398-10-NF) | 2.92 |
| Copovidone, NF (Kollidon VA64) | 3.57 |
| Muco-Adhesive Coating | |
| Amino-Methacrylic Acid Copolymer, NF (EUDRAGIT E100) | 6.38 |
| Talc | 0.64 |
| Enteric Coating | |
| Methacrylic Acid Copolymer, Type A, NF (EUDRAGIT L100) | 3.32 |
| Triethyl Citrate, NF | 0.95 |
| Talc, UPS | 0.47 |
| Blend | |
| Talc | 0.50 |

Example 10

The immediate release component of Example 6 and the controlled release beads of Example 9 were blended to create a mixture with 68.11 wt % controlled release beads and 31.89% immediate release granules. The mixture was filled into hard gelatin capsules containing (a) 180 mg LD and 45 mg CD and (b) 270 mg LD and 67.5 mg CD. The CD weight is based on CD anhydrous.

Example 11

Controlled release particles (beads) with the following composition were prepared according to the procedure of Example 7:

| | Wt % |
|---|---|
| Core | |
| Levodopa USP | 61.83 |
| Microcrystalline Cellulose, NF (Avicel PH-101) | 8.36 |
| Mannitol, USP (Mannogern TM 2080 Granular) | 8.36 |
| Sodium Lauryl Sulfate | 4.18 |
| Povidone | 0.84 |
| Controlled Release Coat | |
| Cellulose acetate, NF (CA-398-10-NF) | 1.88 |
| Copovidone, NF (Kollidon VA64) | 2.30 |
| Muco-Adhesive Coating | |
| Amino-Methacrylic Acid Copolymer, NF (EUDRAGIT E100) | 6.38 |
| Talc | 0.64 |
| Enteric Coating | |
| Methacrylic Acid Copolymer, Type A, NF (EUDRAGIT L100) | 3.31 |
| Triethyl Citrate, NF | 0.95 |
| Talc, UPS | 0.47 |
| Blend | |
| Talc | 0.50 |

Example 12

The immediate release component of Example 6 and the controlled release beads of Example 11 were blended to create a mixture with 67.5 wt % controlled release beads and 32.5% immediate release granules. The mixture was filled into hard gelatin capsules containing (a) 140 mg LD and 35 mg CD; (b) 210 mg LD and 52.5 mg CD; (c) 280 mg LD and 70 mg CD; and (d) 350 mg LD and 87.5 mg CD. The CD weight is based on CD anhydrous. These dosage forms contained approximately 25% of the total LD content in the immediate release component; 75% of the total LD content in the controlled release component and 100% of the total CD content in the immediate release component.

The 210 mg LD and 52.5 mg CD; 280 mg LD and 70 mg CD; and 350 mg LD and 87.5 mg CD capsules prepared in this Example were tested using a USP Type I apparatus, at 37° C.±0.5° C., with a rotational speed of 75 rpms and 900 ml of simulated gastric fluid for 2 hours and pH 6.8 phosphate buffer thereafter. The 140 mg LD and 35 mg CD capsules prepared in this Example were tested using a USP Type I apparatus, at 37° C.±0.5° C., with a rotational speed of 75 rpms and 900 ml of simulated gastric fluid for 2 hours and pH 6.8 phosphate buffer thereafter. The results of the in vitro dissolution testing were as follows:

| | Time | 140/35 mg | | 210/52.5 mg | | 280/70 mg | | 350/87.5 mg | |
|---|---|---|---|---|---|---|---|---|---|
| | (hour) | CD | LD | CD | LD | CD | LD | CD | LD |
| acid | 0.5 | 103 | 28 | 103 | 29 | 103 | 29 | 103 | 29 |
| | 2 | 103 | 40 | 103 | 41 | 103 | 42 | 103 | 42 |
| buffer | 3 | | 68 | | 61 | | 63 | | 67 |
| | 4 | | 85 | | 80 | | 81 | | 86 |
| | 5 | | 94 | | 90 | | 92 | | 95 |
| | 7 | | 97 | | 96 | | 97 | | 99 |
| | 8 | | 97 | | 97 | | 98 | | 100 |
| | 10 | | 97 | | 99 | | 98 | | 100 |

The invention illustratively described herein suitably may be practiced in the absence of any element or elements, limitation or limitations which is not specifically disclosed herein. Thus, for example, in each instance herein, any of the terms "comprising," "consisting essentially of" and "consisting of" may be replaced with either of the other two terms. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A multiparticulate controlled release levodopa solid oral dosage form comprising:
    (i) one or more immediate release levodopa components; and
    (ii) one or more controlled release levodopa particles wherein the one or more controlled release levodopa particles comprise:
        (a) a spheronized core comprising levodopa and at least one pharmaceutically acceptable excipient;
        (b) a coating surrounding the core comprising a muco-adhesive material; and (c) a coating comprising an enteric material surrounding the coating comprising the muco-adhesive material.

2. The dosage form of claim 1 wherein the one or more controlled release particles pass through a 12 mesh screen but are retained on a 25 mesh screen.

3. The dosage form of claim 1 wherein the one or more controlled release particles pass through a 14 mesh screen but are retained on a 24 mesh screen.

4. The dosage form of claim 1 wherein the one or more controlled release particles comprise an extruded and spheronized core.

5. The dosage form of claim 1 wherein the immediate release levodopa components comprise levodopa and is a powder, coating, mini-tablet, bead, pellet, granule or combination thereof.

6. The dosage form of claim 5 wherein the immediate release levodopa components comprise a powder or a granule.

7. The dosage form of claim 5 wherein the immediate release levodopa components comprise a coating applied to one or more of the controlled release levodopa particles.

8. The dosage form of claim 1, wherein the muco-adhesive material is selected from the group consisting of amino methacrylate copolymers, polycarbophil, carbomer, cellulosics, chitosan, diethylaminodextran, diethylaminoethyldextran, polygalactosamine, polylysine, polyomithine, prolamine, polyimine, hyaluronic acid, sodium alginate, sodium carboxymethylcellulose, alginate or a combination thereof.

9. The dosage form of claim 8, wherein the muco-adhesive material is an amino methacrylate copolymer.

10. The dosage form of claim 8, wherein the amino methacrylate copolymer is poly(butyl methacrylate-co-(2-dimethylaminoethyl) methacrylate-co-methyl methacrylate polymer.

11. The dosage form of claim 1, wherein the enteric material dissolves at a pH of greater than or equal to 5.5.

12. The dosage form of claim 11 wherein the enteric material comprises a methacrylic acid copolymer.

13. The dosage form of claim 1 wherein the core of the one or more controlled release particles comprises a mixture of levodopa and one or more pharmaceutically acceptable excipients selected from the group consisting of lubricants, fillers, binders, disintegrants, glidants, surfactants, pH adjusting agents, antioxidants or mixtures of the foregoing.

14. The dosage form of claim 1 wherein the core of the one or more controlled release particles comprises a mixture of levodopa, one or more fillers, one or more binders, and one or more surfactants.

15. The dosage form of claim 1 wherein dosage form releases at least 90% of the levodopa in approximately 5 to 7 hours when tested in a United States Pharmacopeia (USP) Type I dissolution apparatus at 37° C. with a rotational speed of 75 rpms and 900 mL of simulated gastric fluid with a pH of 1.0 for 2 hours followed by simulated intestinal fluid with a pH of 7.0.

16. The dosage form of claim 1 wherein the one or more controlled release particles further comprises a controlled release coating surrounding the core and wherein the controlled release coating is applied prior to the coating (b) comprising the muco-adhesive material.

17. The dosage form of claim 1 further comprising carbidopa.

18. The dosage form of claim 1 comprising about 95 mg to about 390 mg of levodopa.

19. The dosage form of claim 18 comprising about 140 mg of levodopa and about 35 mg of carbidopa.

20. The dosage form of claim 18 comprising about 210 mg of levodopa and about 52.5 mg of carbidopa.

21. The dosage form of claim 18 comprising about 280 mg of levodopa and about 70 mg of carbidopa.

22. The dosage form of claim 18 comprising about 350 mg levodopa and about 87.5 mg of carbidopa.

23. The dosage form of claim 1 wherein the one or more controlled release particles pass through a 12 mesh screen but are retained on a 25 mesh screen; the core of the one or more controlled release particles comprises an extruded and spheronized mixture of levodopa and one or more pharmaceutically acceptable excipients selected from the group consisting of lubricants, fillers, binders, disintegrants, glidants, surfactants, pH adjusting agents, antioxidants or mixtures of the foregoing and the dosage form comprises about 95 mg to about 390 mg of levodopa.

24. A capsule comprising:
(i) one or more immediate release levodopa components; and
(ii) a plurality of controlled release levodopa particles comprising:
(a) a spheronized core comprising levodopa, one or more fillers and one or more binders;
(b) a controlled release coating surrounding the spheronized core;
(c) a muco-adhesive coating comprising a poly(butyl methacrylate-co-(2-dimethylaminoethyl) methacrylate-co-methyl methacrylate polymer surrounding the controlled release coating; and
(d) an enteric coating comprising a methacrylic acid copolymer that dissolves at a pH of 5.5 or greater surrounding the muco-adhesive coating.

25. The capsule of claim 24 wherein the one or more controlled release particles pass through a 12 mesh screen but are retained on a 25 mesh screen.

26. The capsule of claim 24 wherein the one or more controlled release particles pass through a 14 mesh screen but are retained on a 24 mesh screen.

27. The capsule of claim 24 wherein the one or more controlled release particles comprise an extruded and spheronized core comprising levodopa, one or more fillers, one or more binders, and one or more surfactants.

28. The capsule of claim 24 comprising about 95 mg to about 390 mg of levodopa.

29. The capsule of claim 24 wherein the immediate release levodopa components comprise levodopa and is a powder, coating, mini-tablet, bead, pellet, granule or combination thereof.

30. The capsule of claim 29 wherein the immediate release levodopa components comprises a powder or granule.

31. The capsule of claim 24 wherein the immediate release levodopa components comprise one or more granules comprising a mixture of levodopa, carbidopa and one or more pharmaceutically acceptable excipients selected from the group consisting of lubricants, fillers, binders, disintegrants, glidants, surfactants, pH adjusting agents, antioxidants or mixtures of the foregoing.

32. The capsule of claim 31 wherein the one or more immediate release granules comprise a mixture of levodopa, carbidopa, croscarmellose sodium, povidone and magnesium stearate.

33. The capsule of claim 29 wherein the immediate release levodopa components comprise a coating applied to one or more of the controlled release particles.

34. The capsule of claim 24 wherein the controlled release coating comprises ethylcellulose.

35. The capsule of claim 24 wherein the controlled release coating comprises cellulose acetate.

36. The capsule of claim 24 wherein the plurality of controlled release levodopa particles pass through a 14 mesh screen but are retained on a 24 mesh screen and comprise:
   (a) a spheronized core comprising levodopa, microcrystalline cellulose, mannitol, sodium lauryl sulfate and povidone;
   (b) a controlled release coating surrounding the spheronized core wherein the controlled release coating comprises cellulose acetate or ethylcellulose;
   (c) a muco-adhesive coating comprising a poly(butyl-methacrylate-co-(2-dimethylaminoethyl) methacrylate-co-methyl methacrylate polymer surrounding the controlled release coating; and
   (d) an enteric coating comprising a methacrylic acid copolymer that dissolves at a pH of 5.5 or greater surrounding the muco-adhesive coating.

37. The capsule of claim 36 wherein the one or more immediate release levodopa components comprise one or more immediate release granules comprising a mixture of levodopa, carbidopa, one or more disintegrants and one or more binders.

38. The capsule of claim 37 wherein the one or more immediate release granules comprise a mixture of levodopa, carbidopa, croscarmellose sodium, povidone and magnesium stearate.

39. The capsule of claim 36 wherein the plurality of controlled release levodopa particles comprise an extruded and spheronized core comprising levodopa, microcrystalline cellulose, mannitol, sodium lauryl sulfate and povidone.

40. A capsule comprising:
   (i) one or more immediate release levodopa components; and
   (ii) a plurality of controlled release levodopa particles comprising:
      (a) an extruded spheronized core comprising levodopa, one or more fillers, and one or more binders;
      (b) a controlled release coating surrounding the spheronized core;
      (c) a muco-adhesive coating comprising a poly(butyl methacrylate-co-(2-dimethylaminoethyl) methacrylate-co-methyl methacrylate polymer surrounding the controlled release coating; and
      (d) an enteric coating comprising a methacrylic acid copolymer that dissolves at a pH of 5.5 or greater surrounding the muco-adhesive coating;
   wherein the controlled release levodopa particles pass through a 12 mesh screen but are retained on a 25 mesh screen and the capsule contains about 95 mg to about 390 mg of levodopa.

* * * * *